United States Patent
Li et al.

(10) Patent No.: US 11,649,270 B2
(45) Date of Patent: May 16, 2023

(54) T-CELL RECEPTOR RECOGNIZING SSX2 ANTIGEN

(71) Applicant: XLIFESC, LTD., Guandong (CN)

(72) Inventors: Yi Li, Guangdong (CN); Jing Hu, Guangdong (CN); Jun Li, Guangdong (CN); Hanli Sun, Guangdong (CN)

(73) Assignee: XLIFESC, LTD., Guangdong (CN)

( * ) Notice: Subject to any disclaimer, the term of this patent is extended or adjusted under 35 U.S.C. 154(b) by 35 days.

(21) Appl. No.: 17/279,372

(22) PCT Filed: Sep. 20, 2019

(86) PCT No.: PCT/CN2019/107097
§ 371 (c)(1),
(2) Date: Mar. 24, 2021

(87) PCT Pub. No.: WO2020/063488
PCT Pub. Date: Apr. 2, 2020

(65) Prior Publication Data
US 2021/0395330 A1    Dec. 23, 2021

(30) Foreign Application Priority Data

Sep. 26, 2018 (CN) .......................... 201811123747.0

(51) Int. Cl.
*C07K 14/725* (2006.01)
*A61K 38/00* (2006.01)

(52) U.S. Cl.
CPC .......... *C07K 14/7051* (2013.01); *A61K 38/00* (2013.01)

(58) Field of Classification Search
CPC ... C07K 14/7051; A61P 35/00; C12N 5/0636; A61K 35/17; A61K 38/00
See application file for complete search history.

(56) References Cited

U.S. PATENT DOCUMENTS

2007/0060524 A1    3/2007  Liu et al.
2013/0274203 A1*  10/2013  Morgan ................. A61P 21/00
                                                514/19.5

FOREIGN PATENT DOCUMENTS

| CN | 101273056 A | 9/2008 | |
| JP | 2017081836 A * | 5/2017 | |
| WO | WO-2019133853 A1 * | 7/2019 | ............. A61P 35/00 |

OTHER PUBLICATIONS

Schamel et al, "Coexistence of multivalent and monovalent TCRs explains high sensitivity and wide range of response", 2005, JEM, vol. 202, No. 4, 493-503 (Year: 2005).*

(Continued)

*Primary Examiner* — Joanne Hama
*Assistant Examiner* — Jessica Soto-Rodriguez
(74) *Attorney, Agent, or Firm* — Mintz Levin Cohn Ferris Glovsky and Popeo, P.C.

(57) ABSTRACT

A T cell receptor (TCR) capable of specifically binding to a short peptide KASEKIFYV derived from an AFP antigen. The antigen short peptide KASEKIFYV can form a complex with HLA A0201 and be presented together with same to the cell surface. A nucleic acid molecule encoding the TCR, a vector comprising the nucleic acid molecule, and a cell that transduces the TCR.

26 Claims, 9 Drawing Sheets

Specification includes a Sequence Listing.

(56) References Cited

OTHER PUBLICATIONS

Abate-Daga, "Development of a T Cell Receptor Targeting an HLAA*0201 Restricted Epitope from the Cancer-Testis Antigen SSX2 for Adoptive Immunotherapy of Cancer", 2014, PLOS One, vol. 9, Issue 3 (Year: 2014).*
International Search Report dated Nov. 25, 2019 corresponding to PCT/CN2019/107097 filed Sep. 20, 2019; 3 pages.
De Simone, Marco et al., "Single Cell T Cell Receptor Sequencing: Techniques and Future Challenges," *Frontiers in Immunology* (Jul. 18, 2018); vol. 9, Article 1638; 7 pages.

* cited by examiner

FIG. 1A

AQTVTQSQPEMSVQEAETVTLSCTYDTSESDYYLFWYKQPPSRQMILVIRQEAY
KQQNATENRFSVNFQKAAKSFSLKISDSQLGDAAMYFCAYRSGIIQGAQKLVFG
QGTRLTINPN (SEQ ID NO.1)

FIG. 1B gctcagacagtcactcagtctcaaccagagatgtctgtgcaggaggcagagaccgtgaccctgagctgcacatatgacacc
agtgagagtgattattatttattctggtacaagcagcctcccagcaggcagatgattctcgttattcgccaagaagcttataagc
aacagaatgcaacagagaatcgtttctctgtgaacttccagaaagcagccaaatccttcagtctcaagatctcagactcacag
ctgggggatgccgcgatgtatttctgtgcttataggagcggcataattcagggagcccagaagctggtatttggccaaggaa
ccaggctgactatcaacccaaat (SEQ ID NO.2)

FIG. 1C

AQTVTQSQPEMSVQEAETVTLSCTYDTSESDYYLFWYKQPPSRQMILVIRQEAY
KQQNATENRFSVNFQKAAKSFSLKISDSQLGDAAMYFCAYRSGIIQGAQKLVFG
QGTRLTINPNIQNPDPAVYQLRDSKSSDKSVCLFTDFDSQTNVSQSKDSDVYITD
KTVLDMRSMDFKSNSAVAWSNKSDFACANAFNNSIIPEDTFFPSPESSCDVKLV
EKSFETDTNLNFQNLSVIGFRILLLKVAGFNLLMTLRLWSS (SEQ ID NO.3)

FIG. 1D gctcagacagtcactcagtctcaaccagagatgtctgtgcaggaggcagagaccgtgaccctgagctgcacatatgacacc
agtgagagtgattattatttattctggtacaagcagcctcccagcaggcagatgattctcgttattcgccaagaagcttataagc
aacagaatgcaacagagaatcgtttctctgtgaacttccagaaagcagccaaatccttcagtctcaagatctcagactcacag
ctgggggatgccgcgatgtatttctgtgcttataggagcggcataattcagggagcccagaagctggtatttggccaaggaa
ccaggctgactatcaacccaaatAtccagaaccctgaccctgccgtgtaccagctgagagactctaaatccagtgacaagt
ctgtctgcctattcaccgattttgattctcaaacaaatgtgtcacaaagtaaggattctgatgtgtatatcacagacaaaactgtg
ctagacatgaggtctatggacttcaagagcaacagtgctgtggcctggagcaacaaatctgactttgcatgtgcaaacgcctt
caacaacagcattattccagaagacaccttcttccccagcccagaaagttcctgtgatgtcaagctggtcgagaaaagctttg
aaacagatacgaacctaaactttcaaaacctgtcagtgattgggttccgaatcctcctcctgaaagtggccgggtttaatctgc
tcatgacgctgcggctgtggtccagcTAA (SEQ ID NO.4)

FIG. 1E

MACPGFLWALVISTCLEFSMAQTVTQSQPEMSVQEAETVTLSCTYDTSESDYYL
FWYKQPPSRQMILVIRQEAYKQQNATENRFSVNFQKAAKSFSLKISDSQLGDAA
MYFCAYRSGIIQGAQKLVFGQGTRLTINPNIQNPDPAVYQLRDSKSSDKSVCLFT
DFDSQTNVSQSKDSDVYITDKTVLDMRSMDFKSNSAVAWSNKSDFACANAFN
NSIIPEDTFFPSPESSCDVKLVEKSFETDTNLNFQNLSVIGFRILLLKVAGFNLLMT
LRLWSS (SEQ ID NO.22)

FIG. 1F atggcatgccctggcttcctgtgggcacttgtgatctccacctgtcttgaatttagcatggctcagacagtcactcagtctcaac
cagagatgtctgtgcaggaggcagagaccgtgaccctgagctgcacatatgacaccagtgagagtgattattatttattctgg
tacaagcagcctcccagcaggcagatgattctcgttattcgccaagaagcttataagcaacagaatgcaacagagaatcgtt
tctctgtgaacttccagaaagcagccaaatccttcagtctcaagatctcagactcacagctgggggatgccgcgatgtatttct
gtgcttataggagcggcataattcagggagcccagaagctggtatttggccaaggaaccaggctgactatcaacccaaatA
tccagaaccctgaccctgccgtgtaccagctgagagactctaaatccagtgacaagtctgtctgcctattcaccgattttgatt
ctcaaacaaatgtgtcacaaagtaaggattctgatgtgtatatcacagacaaaactgtgctagacatgaggtctatggacttca
agagcaacagtgctgtggcctggagcaacaaatctgactttgcatgtgcaaacgccttcaacaacagcattattccagaaga
caccttcttccccagcccagaaagttcctgtgatgtcaagctggtcgagaaaagctttgaaacagatacgaacctaaactttc
aaaacctgtcagtgattgggttccgaatcctcctcctgaaagtggccgggtttaatctgctcatgacgctgcggctgtggtcca
gcTAA (SEQ ID NO.23)

FIG. 2A

AAGVIQSPRHLIKEKRETATLKCYPI<u>PRHDT</u>VYWYQQGPGQDPQFLIS<u>FYEKMQ</u>
SDKGSIPDRFSAQQFSDYHSELNMSSLELGDSALYFC<u>ASSSDRELLFYNEQFF</u>GP
GTRLTVL (SEQ ID NO.5)

FIG. 2B gctgctggagtcatccagtccccaagacatctgatcaaagaaaagagggaaacagccactctgaaatgctatcctatcccta
gacacgacactgtctactggtaccagcagggtccaggtcaggaccccccagttcctcatttcgttttatgaaaagatgcagag
cgataaaggaagcatccctgatcgattctcagctcaacagttcagtgactatcattctgaactgaacatgagctccttggagct
gggggactcagccctgtacttctgtgccagcagctcagacagggaactattattctacaatgagcagttcttcgggccaggg
acacggctcaccgtgcta (SEQ ID NO.6)

FIG. 2C

AAGVIQSPRHLIKEKRETATLKCYPIPRHDTVYWYQQGPGQDPQFLISFYEKMQ
SDKGSIPDRFSAQQFSDYHSELNMSSLELGDSALYFCASSSDRELLFYNEQFFGP
GTRLTVLEDLKNVFPPEVAVFEPSEAEISHTQKATLVCLATGFYPDHVELSWWV
NGKEVHSGVSTDPQPLKEQPALNDSRYCLSSRLRVSATFWQNPRNHFRCQVQF
YGLSENDEWTQDRAKPVTQIVSAEAWGRADCGFTSESYQQGVLSATILYEILLG
KATLYAVLVSALVLMAMVKRKDSRG (SEQ ID NO.7)

FIG. 2D gctgctggagtcatccagtccccaagacatctgatcaaagaaaagagggaaacagccactctgaaatgctatcctatcccta
gacacgacactgtctactggtaccagcagggtccaggtcaggaccccagttcctcatttcgttttatgaaaagatgcagag
cgataaaggaagcatccctgatcgattctcagctcaacagttcagtgactatcattctgaactgaacatgagctccttggagct
gggggactcagccctgtacttctgtgccagcagctcagacagggaactattattctacaatgagcagttcttcgggccaggg
acacggctcaccgtgctaGaggacctgaaaaacgtgttcccacccgaggtcgctgtgtttgagccatcagaagcagagat
ctcccacacccaaaaggccacactggtgtgcctggccacaggcttctaccccgaccacgtggagctgagctggtgggtga
atgggaaggaggtgcacagtggggtcagcacagacccgcagcccctcaaggagcagcccgccctcaatgactccagat
actgcctgagcagccgcctgagggtctcggccaccttctggcagaaccccgcaaccacttccgctgtcaagtccagttcta
cgggctctcggagaatgacgagtggacccaggatagggccaaacctgtcacccagatcgtcagcgccgaggcctggggt
agagcagactgtggcttcacctccgagtcttaccagcaagggtcctgtctgccaccatcctctatgagatcttgctagggaa
ggccaccttgtatgccgtgctggtcagtgccctcgtgctgatggccatggtcaagagaaaggattccagaggcTAA
(SEQ ID NO.8)

FIG. 2E

MLSPDLPDSAWNTRLLCRVMLCLLGAGSVAAGVIQSPRHLIKEKRETATLKCY
PIPRHDTVYWYQQGPGQDPQFLISFYEKMQSDKGSIPDRFSAQQFSDYHSELNM
SSLELGDSALYFCASSSDRELLFYNEQFFGPGTRLTVLEDLKNVFPPEVAVFEPS
EAEISHTQKATLVCLATGFYPDHVELSWWVNGKEVHSGVSTDPQPLKEQPALN
DSRYCLSSRLRVSATFWQNPRNHFRCQVQFYGLSENDEWTQDRAKPVTQIVSA
EAWGRADCGFTSESYQQGVLSATILYEILLGKATLYAVLVSALVLMAMVKRKD
SRG (SEQ ID NO.24)

FIG. 2F

Atgcttagtcctgacctgcctgactctgcctggaacaccaggctcctctgccgtgtcatgctttgtctcctgggagcaggttca
gtggctgctggagtcatccagtccccaagacatctgatcaaagaaaagagggaaacagccactctgaaatgctatcctatcc
ctagacacgacactgtctactggtaccagcagggtccaggtcaggaccccagttcctcatttcgttttatgaaaagatgcag
agcgataaaggaagcatccctgatcgattctcagctcaacagttcagtgactatcattctgaactgaacatgagctccttgga
gctgggggactcagccctgtacttctgtgccagcagctcagacagggaactattattctacaatgagcagttcttcgggcca
gggacacggctcaccgtgctaGaggacctgaaaaacgtgttcccacccgaggtcgctgtgtttgagccatcagaagcaga
gatctcccacacccaaaaggccacactggtgtgcctggccacaggcttctaccccgaccacgtggagctgagctggtggg
tgaatgggaaggaggtgcacagtggggtcagcacagacccgcagcccctcaaggagcagcccgccctcaatgactcca
gatactgcctgagcagccgcctgagggtctcggccaccttctggcagaaccccgcaaccacttccgctgtcaagtccagt
tctacgggctctcggagaatgacgagtggacccaggatagggccaaacctgtcacccagatcgtcagcgccgaggcctg
gggtagagcagactgtggcttcacctccgagtcttaccagcaagggtcctgtctgccaccatcctctatgagatcttgctag
ggaaggccaccttgtatgccgtgctggtcagtgccctcgtgctgatggccatggtcaagagaaaggattccagaggcTA
A (SEQ ID NO.25)

FIG. 3

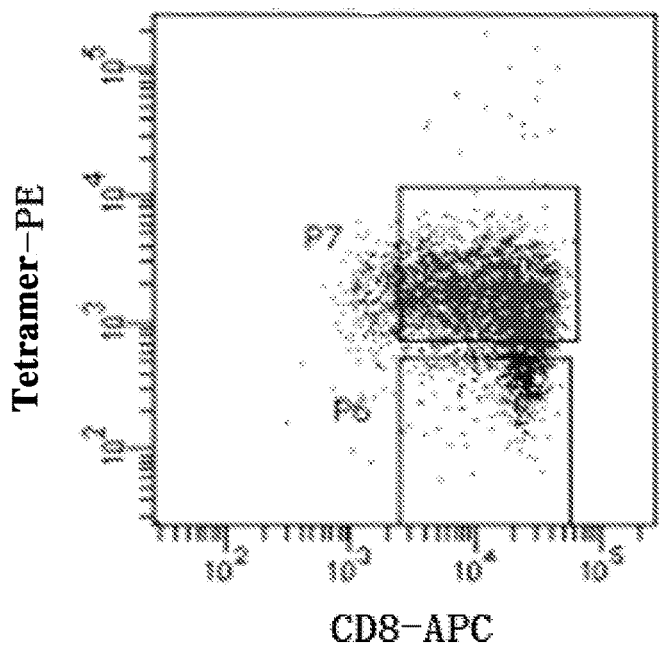

FIG. 4A

MAQTVTQSQPEMSVQEAETVTLSCTYDTSESDYYLFWYKQPPSRQMILVIRQEA
YKQQNATENRFSVNFQKAAKSFSLKISDSQLGDAAMYFCAYRSGIIQGAQKLVF
GQGTRLTINPNIQNPDPAVYQLRDSKSSDKSVCLFTDFDSQTNVSQSKDSDVYIT
DKCVLDMRSMDFKSNSAVAWSNKSDFACANAFNNSIIPEDTFFPSPESS (SEQ ID
NO.26)

FIG. 4B

ATGGCGCAGACCGTGACCCAGTCTCAACCAGAGATGTCTGTGCAGGAGGCA
GAGACCGTGACCCTGAGCTGCACATATGACACCAGTGAGAGTGATTATTATT
TATTCTGGTACAAGCAGCCTCCCAGCAGGCAGATGATTCTCGTTATTCGCCA
AGAAGCTTATAAGCAACAGAATGCAACAGAGAATCGTTTCTCTGTGAACTT
CCAGAAAGCAGCCAAATCCTTCAGTCTCAAGATCTCAGACTCACAGCTGGG
GGATGCCGCGATGTATTTCTGTGCTTATAGGAGCGGCATAATTCAGGGAGCC
CAGAAGCTGGTATTTGGCCAAGGAACCAGGCTGACTATCAACCCAAATATC
CAGAACCCTGACCCTGCCGTGTACCAGCTGAGAGACTCTAAGTCGAGTGAC
AAGTCTGTCTGCCTATTCACCGATTTTGATTCTCAAACAAATGTGTCACAAA
GTAAGGATTCTGATGTGTATATCACAGACAAATGTGTGCTAGACATGAGGTC
TATGGACTTCAAGAGCAACAGTGCTGTGGCCTGGAGCAACAAATCTGACTTT
GCATGTGCAAACGCCTTCAACAACAGCATTATTCCAGAAGACACCTTCTTCC
CCAGCCCAGAAAGTTCC (SEQ ID NO.27)

FIG. 5A

MAAGVIQSPRHLIKEKRETATLKCYPIPRHDTVYWYQQGPGQDPQFLISFYEKM
QSDKGSIPDRFSAQQFSDYHSELNMSSLELGDSALYFCASSSDRELLFYNEQFFG
PGTRLTVLEDLKNVFPPEVAVFEPSEAEISHTQKATLVCLATGFYPDHVELSWW
VNGKEVHSGVCTDPQPLKEQPALNDSRYALSSRLRVSATFWQDPRNHFRCQVQ
FYGLSENDEWTQDRAKPVTQIVSAEAWGRAD (SEQ ID NO.28)

FIG. 5B

ATGGCGGCGGGCGTGATTCAGTCCCCAAGACATCTGATCAAAGAAAAGAGG
GAAACAGCCACTCTGAAATGCTATCCTATCCCTAGACACGACACTGTCTACT
GGTACCAGCAGGGTCCAGGTCAGGACCCCCAGTTCCTCATTTCGTTTTATGA
AAAGATGCAGAGCGATAAAGGAAGCATCCCTGATCGATTCTCAGCTCAACA
GTTCAGTGACTATCATTCTGAACTGAACATGAGCTCCTTGGAGCTGGGGGAC
TCAGCCCTGTACTTCTGTGCCAGCAGCTCAGACAGGGAACTATTATTCTACA
ATGAGCAGTTCTTCGGGCCAGGGACACGGCTCACCGTGCTAGAGGACCTGA
AAAACGTGTTCCCACCCGAGGTCGCTGTGTTTGAGCCATCAGAAGCAGAGA
TCTCCCACACCCAAAAGGCCACACTGGTGTGCCTGGCCACCGGTTTCTACCC
CGACCACGTGGAGCTGAGCTGGTGGGTGAATGGGAAGGAGGTGCACAGTGG
GGTCTGCACAGACCCGCAGCCCCTCAAGGAGCAGCCCGCCCTCAATGACTC
CAGATACGCTCTGAGCAGCCGCCTGAGGGTCTCGGCCACCTTCTGGCAGGA
CCCCCGCAACCACTTCCGCTGTCAAGTCCAGTTCTACGGGCTCTCGGAGAAT
GACGAGTGGACCCAGGATAGGGCCAAACCCGTCACCCAGATCGTCAGCGCC
GAGGCCTGGGGTAGAGCAGAC (SEQ ID NO.29)

FIG. 6

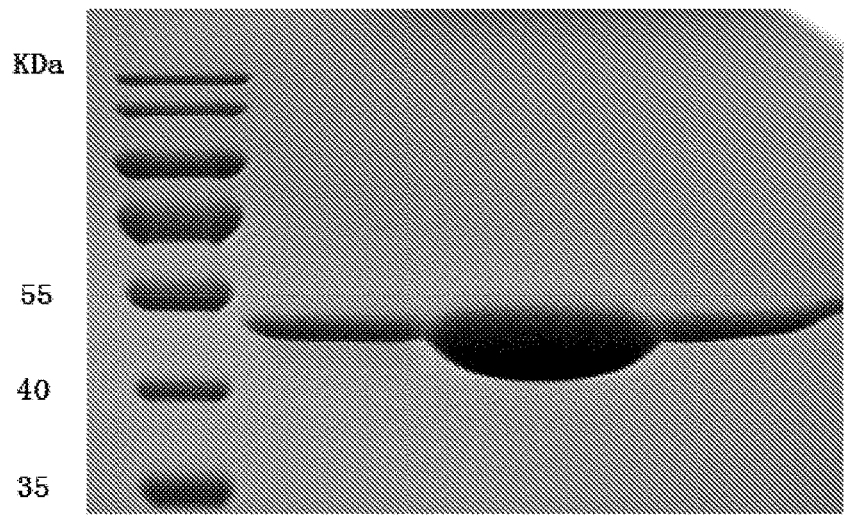

FIG. 7A

MAQTVTQSQPELSVQEGETVTISCTYDTSESDYYLFWYKQPPSRQPILVIRQEAY
KQQNATENRFSVNFQKAAKSFSLKISDVQPGDAAMYFCAYRSGIIQGAQKLVF
GQGTRLTINP<u>GGGSEGGGSEGGGSEGGGSEGG</u>TGAAGVTQSPRHLSVEKGETV
TLKCYPIPRHDTVYWYQQGPGQDLQFLISFYEKMQSDKGSIPDRFSAQQFSDYH
SELNISSVEPGDSALYFCASSSDRELLFYNEQFFGPGTRLTVD (SEQ ID NO.30)

FIG. 7B

ATGGCTCAaACtGTtACtCAGAGCCAACCGGAGCTGAGCGTGCAAGAGGGTGA
AACCGTTACCATCAGCTGCACCTACGACACCAGCGAAAGCGATTACTACCT
GTTCTGGTATAAGCAGCCGCCGAGCCGTCAACCGATCCTGGTTATTCGTCAG
GAAGCGTACAAACAGCAAAACGCGACCGAAAACCGTTTCAGCGTGAACTTT
CAGAAGGCGGCGAAAAGCTTCAGCCTGAAGATCAGCGACGTTCAACCGGGC
GATGCGGCGATGTACTTTTGCGCGTATCGTAGCGGTATCATTCAGGGCGCGC
AAAAACTGGTGTTCGGTCAGGGCACCCGTCTGACCATTAACCCGGGTGGCG
GTAGCGAGGGCGGTGGCAGCGAAGGTGGCGGTAGCGAGGGCGGTGGCAGC
GAAGGTGGCACCGGTGCGGCGGGCGTGACCCAAAGCCCGCGTCACCTGAGC
GTGGAGAAGGGTGAAACCGTTACCCTGAAATGCTATCCGATCCCGCGTCAC
GACACCGTTTACTGGTATCAGCAAGGTCCGGGCCAGGATCTGCAATTCCTGA
TCAGCTTTTACGAAGATGCAGAGCGACAAAGGTAGCATTCCGGATCGTT
TCAGCGCGCAGCAATTTAGCGACTATCACAGCGAGCTGAACATTAGCAGCG
TGGAACCGGGTGACAGCGCGCTGTACTTCTGCGCGAGCAGCAGCGATCGTG
AGCTGCTGTTTTATAACGAACAGTTCTTTGGTCCGGGCACCCGTCTGACCGT
TGAT (SEQ ID NO.31)

FIG. 8A

MAQTVTQSQPELSVQEGETVTISCTYDTSESDYYLFWYKQPPSRQPILVIRQEAY
KQQNATENRFSVNFQKAAKSFSLKISDVQPGDAAMYFCAYRSGIIQGAQKLVF
GQGTRLTINP (SEQ ID NO.32)

FIG. 8B

ATGGCTCAaACtGTtACtCAGAGCCAACCGGAGCTGAGCGTGCAAGAGGGTGA
AACCGTTACCATCAGCTGCACCTACGACACCAGCGAAAGCGATTACTACCT
GTTCTGGTATAAGCAGCCGCCGAGCCGTCAACCGATCCTGGTTATTCGTCAG
GAAGCGTACAAACAGCAAAACGCGACCGAAAACCGTTTCAGCGTGAACTTT
CAGAAGGCGGCGAAAAGCTTCAGCCTGAAGATCAGCGACGTTCAACCGGGC
GATGCGGCGATGTACTTTTGCGCGTATCGTAGCGGTATCATTCAGGGCGCGC
AAAAACTGGTGTTCGGTCAGGGCACCCGTCTGACCATTAACCCG (SEQ ID
NO.33)

FIG. 9A

AAGVTQSPRHLSVEKGETVTLKCYPIPRHDTVYWYQQGPGQDLQFLISFYEKM
QSDKGSIPDRFSAQQFSDYHSELNISSVEPGDSALYFCASSSDRELLFYNEQFFGP
GTRLTVD (SEQ ID NO.34)

FIG. 9B

GCGGCGGGCGTGACCCAAAGCCCGCGTCACCTGAGCGTGGAGAAGGGTGAA
ACCGTTACCCTGAAATGCTATCCGATCCCGCGTCACGACACCGTTTACTGGT
ATCAGCAAGGTCCGGGCCAGGATCTGCAATTCCTGATCAGCTTTTACGAGAA
GATGCAGAGCGACAAAGGTAGCATTCCGGATCGTTTCAGCGCGCAGCAATT
TAGCGACTATCACAGCGAGCTGAACATTAGCAGCGTGGAACCGGGTGACAG
CGCGCTGTACTTCTGCGCGAGCAGCAGCGATCGTGAGCTGCTGTTTTATAAC
GAACAGTTCTTTGGTCCGGGCACCCGTCTGACCGTTGAT (SEQ ID NO.35)

FIG. 10A

GGGSEGGGSEGGGSEGGGSEGGTG (SEQ ID NO.36)

FIG. 10B

GGTGGCGGTAGCGAGGGCGGTGGCAGCGAAGGTGGCGGTAGCGAGGGCGG
TGGCAGCGAAGGTGGCACCGGT (SEQ ID NO.37)

FIG. 11

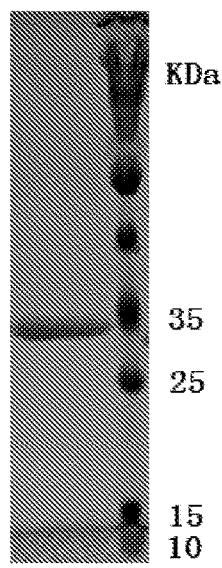

SEQUENCE LISTING

<160> NUMBER OF SEQ ID NOS: 37

<210> SEQ ID NO 1
<211> LENGTH: 118
<212> TYPE: PRT
<213> ORGANISM: Artificial sequence
<220> FEATURE:
<223> OTHER INFORMATION: Synthesized polypeptide

<400> SEQUENCE: 1

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

```
Asp Ser Gln Leu Gly Asp Ala Ala Met Tyr Phe Cys Ala Tyr Arg Ser
            85                  90                  95

Gly Ile Ile Gln Gly Ala Gln Lys Leu Val Phe Gly Gln Gly Thr Arg
        100                 105                 110

Leu Thr Ile Asn Pro Asn
        115

<210> SEQ ID NO 2
<211> LENGTH: 354
<212> TYPE: DNA
<213> ORGANISM: Artificial sequence
<220> FEATURE:
<223> OTHER INFORMATION: Synthesized polynucleotide

<400> SEQUENCE: 2
gctcagacag tcactcagtc tcaaccagag atgtctgtgc aggaggcaga gaccgtgacc      60
ctgagctgca catatgacac cagtgagagt gattattatt tattctggta caagcagcct     120
cccagcaggc agatgattct cgttattcgc caagaagctt ataagcaaca gaatgcaaca     180
gagaatcgtt tctctgtgaa cttccagaaa gcagccaaat ccttcagtct caagatctca     240
gactcacagc tggggatgc cgcgatgtat ttctgtgctt ataggagcgg cataattcag     300
ggagcccaga agctggtatt tggccaagga accaggctga ctatcaaccc aaat            354

<210> SEQ ID NO 3
<211> LENGTH: 258
<212> TYPE: PRT
<213> ORGANISM: Artificial sequence
<220> FEATURE:
<223> OTHER INFORMATION: Synthesized polypeptide

<400> SEQUENCE: 3

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
            85                  90                  95

Gly Ile Ile Gln Gly Ala Gln Lys Leu Val Phe Gly Gln Gly Thr Arg
        100                 105                 110

Leu Thr Ile Asn Pro Asn Ile Gln Asn Pro Asp Pro Ala Val Tyr Gln
        115                 120                 125

Leu Arg Asp Ser Lys Ser Ser Asp Lys Ser Val Cys Leu Phe Thr Asp
    130                 135                 140

Phe Asp Ser Gln Thr Asn Val Ser Gln Ser Lys Asp Ser Asp Val Tyr
145                 150                 155                 160

Ile Thr Asp Lys Thr Val Leu Asp Met Arg Ser Met Asp Phe Lys Ser
                165                 170                 175

Asn Ser Ala Val Ala Trp Ser Asn Lys Ser Asp Phe Ala Cys Ala Asn
            180                 185                 190

Ala Phe Asn Asn Ser Ile Ile Pro Glu Asp Thr Phe Phe Pro Ser Pro
        195                 200                 205
```

```
Glu Ser Ser Cys Asp Val Lys Leu Val Glu Lys Ser Phe Glu Thr Asp
    210                 215                 220

Thr Asn Leu Asn Phe Gln Asn Leu Ser Val Ile Gly Phe Arg Ile Leu
225                 230                 235                 240

Leu Leu Lys Val Ala Gly Phe Asn Leu Leu Met Thr Leu Arg Leu Trp
                245                 250                 255

Ser Ser

<210> SEQ ID NO 4
<211> LENGTH: 777
<212> TYPE: DNA
<213> ORGANISM: Artificial sequence
<220> FEATURE:
<223> OTHER INFORMATION: Synthesized polynucleotide

<400> SEQUENCE: 4
gctcagacag tcactcagtc tcaaccagag atgtctgtgc aggaggcaga gaccgtgacc      60
ctgagctgca catatgacac cagtgagagt gattattatt tattctggta caagcagcct     120
cccagcaggc agatgattct cgttattcgc caagaagctt ataagcaaca gaatgcaaca     180
gagaatcgtt tctctgtgaa cttccagaaa gcagccaaat ccttcagtct caagatctca     240
gactcacagc tgggggatgc cgcgatgtat ttctgtgctt ataggagcgg cataattcag     300
ggagcccaga agctggtatt tggccaagga accaggctga ctatcaaccc aaatatccag     360
aaccctgacc ctgccgtgta ccagctgaga gactctaaat ccagtgacaa gtctgtctgc     420
ctattcaccg attttgattc tcaaacaaat gtgtcacaaa gtaaggattc tgatgtgtat     480
atcacagaca aaactgtgct agacatgagg tctatggact caagagcaa cagtgctgtg     540 gcctggagca caaatctga ctttgcatgt gcaaacgcct tcaacaacag cattattcca     600
gaagacacct tcttccccag cccagaaagt tcctgtgatg tcaagctggt cgagaaagc      660 tttgaaacag atacgaacct aaactttcaa aacctgtcag tgattgggtt ccgaatcctc     720
ctcctgaaag tggccgggtt taatctgctc atgacgctgc ggctgtggtc cagctaa       777

<210> SEQ ID NO 5
<211> LENGTH: 116
<212> TYPE: PRT
<213> ORGANISM: Artificial sequence
<220> FEATURE:
<223> OTHER INFORMATION: Synthesized polypeptide

<400> SEQUENCE: 5

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
                20                  25                  30

Tyr Trp Tyr Gln Gln Gly Pro Gly Gln Asp Pro Gln Phe Leu Ile Ser
            35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Leu Phe Tyr Asn Glu Gln Phe Phe Gly Pro Gly Thr Arg
                100                 105                 110
```

Leu Thr Val Leu
        115

<210> SEQ ID NO 6
<211> LENGTH: 348
<212> TYPE: DNA
<213> ORGANISM: Artificial sequence
<220> FEATURE:
<223> OTHER INFORMATION: Synthesized polynucleotide

<400> SEQUENCE: 6

```
gctgctggag tcatccagtc cccaagacat ctgatcaaag aaaagaggga aacagccact      60
ctgaaatgct atcctatccc tagacacgac actgtctact ggtaccagca gggtccaggt     120
caggaccccc agttcctcat ttcgttttat gaaaagatgc agagcgataa aggaagcatc     180
cctgatcgat tctcagctca acagttcagt gactatcatt ctgaactgaa catgagctcc     240
ttggagctgg gggactcagc cctgtacttc tgtgccagca gctcagacag ggaactatta     300
ttctacaatg agcagttctt cgggccaggg acacggctca ccgtgcta                 348
```

<210> SEQ ID NO 7
<211> LENGTH: 295
<212> TYPE: PRT
<213> ORGANISM: Artificial sequence
<220> FEATURE:
<223> OTHER INFORMATION: Synthesized polypeptide

<400> SEQUENCE: 7

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Ser Asp
                85                  90                  95

Arg Glu Leu Leu Phe Tyr Asn Glu Gln Phe Phe Gly Pro Gly Thr Arg
            100                 105                 110

Leu Thr Val Leu Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp Cys Gly Phe Thr Ser Glu Ser Tyr Gln Gln
                245                 250                 255

Gly Val Leu Ser Ala Thr Ile Leu Tyr Glu Ile Leu Leu Gly Lys Ala
            260                 265                 270

Thr Leu Tyr Ala Val Leu Val Ser Ala Leu Val Leu Met Ala Met Val
        275                 280                 285

Lys Arg Lys Asp Ser Arg Gly
    290                 295

<210> SEQ ID NO 8
<211> LENGTH: 888
<212> TYPE: DNA
<213> ORGANISM: Artificial sequence
<220> FEATURE:
<223> OTHER INFORMATION: Synthesized polynucleotide

<400> SEQUENCE: 8
gctgctggag tcatccagtc cccaagacat ctgatcaaag aaaagaggga aacagccact      60
ctgaaatgct atcctatccc tagacacgac actgtctact ggtaccagca gggtccaggt     120 caggacccc agttcctcat ttcgttttat gaaaagatgc agagcgataa aggaagcatc      180
cctgatcgat tctcagctca acagttcagt gactatcatt ctgaactgaa catgagctcc     240
ttggagctgg gggactcagc cctgtacttc tgtgccagca gctcagacag gaactatta     300 ttctacaatg agcagttctt cgggccaggg acacggctca ccgtgctaga ggacctgaaa     360
aacgtgttcc cacccgaggt cgctgtgttt gagccatcag aagcagagat ctcccacacc     420
caaaaggcca cactggtgtg cctggccaca ggcttctacc ccgaccacgt ggagctgagc     480
tggtgggtga atgggaagga ggtgcacagt ggggtcagca gagacccgca gccctcaag     540 gagcagcccg ccctcaatga ctccagatac tgcctgagca gccgcctgag ggtctcggcc     600
accttctggc agaaccccg caaccacttc cgctgtcaag tccagttcta cgggctctcg     660
gagaatgacg agtggaccca ggatagggcc aaacctgtca cccagatcgt cagcgccgag     720
gcctggggta gagcagactg tggcttcacc tccgagtctt accagcaagg ggtcctgtct     780
gccaccatcc tctatgagat cttgctaggg aaggccacct gtatgccgt gctggtcagt      840 gccctcgtgc tgatggccat ggtcaagaga aaggattcca gaggctaa                   888

<210> SEQ ID NO 9
<211> LENGTH: 9
<212> TYPE: PRT
<213> ORGANISM: Artificial sequence
<220> FEATURE:
<223> OTHER INFORMATION: Synthesized polypeptide

<400> SEQUENCE: 9

Lys Ala Ser Glu Lys Ile Phe Tyr Val
1               5

<210> SEQ ID NO 10
<211> LENGTH: 7
<212> TYPE: PRT
<213> ORGANISM: Artificial sequence
<220> FEATURE:
<223> OTHER INFORMATION: Synthesized polypeptide

<400> SEQUENCE: 10

Thr Ser Glu Ser Asp Tyr Tyr
1               5

<210> SEQ ID NO 11
<211> LENGTH: 8
<212> TYPE: PRT
<213> ORGANISM: Artificial sequence
<220> FEATURE:
<223> OTHER INFORMATION: Synthesized polypeptide

<400> SEQUENCE: 11

Gln Glu Ala Tyr Lys Gln Gln Asn
1               5

<210> SEQ ID NO 12
<211> LENGTH: 14
<212> TYPE: PRT
<213> ORGANISM: Artificial sequence
<220> FEATURE:
<223> OTHER INFORMATION: Synthesized polypeptide

<400> SEQUENCE: 12

Ala Tyr Arg Ser Gly Ile Ile Gln Gly Ala Gln Lys Leu Val
1               5                   10

<210> SEQ ID NO 13
<211> LENGTH: 5
<212> TYPE: PRT
<213> ORGANISM: Artificial sequence
<220> FEATURE:
<223> OTHER INFORMATION: Synthesized polypeptide

<400> SEQUENCE: 13

Pro Arg His Asp Thr
1               5

<210> SEQ ID NO 14
<211> LENGTH: 6
<212> TYPE: PRT
<213> ORGANISM: Artificial sequence
<220> FEATURE:
<223> OTHER INFORMATION: Synthesized polypeptide

<400> SEQUENCE: 14

Phe Tyr Glu Lys Met Gln
1               5

<210> SEQ ID NO 15
<211> LENGTH: 15
<212> TYPE: PRT
<213> ORGANISM: Artificial sequence
<220> FEATURE:
<223> OTHER INFORMATION: Synthesized polypeptide

<400> SEQUENCE: 15

Ala Ser Ser Ser Asp Arg Glu Leu Leu Phe Tyr Asn Glu Gln Phe
1               5                   10                  15

<210> SEQ ID NO 16
<211> LENGTH: 21
<212> TYPE: DNA
<213> ORGANISM: Artificial sequence
<220> FEATURE:
<223> OTHER INFORMATION: Synthesized polynucleotide

<400> SEQUENCE: 16
accagtgaga gtgattatta t                                              21

<210> SEQ ID NO 17

```
<211> LENGTH: 24
<212> TYPE: DNA
<213> ORGANISM: Artificial sequence
<220> FEATURE:
<223> OTHER INFORMATION: Synthesized polynucleotide

<400> SEQUENCE: 17
caagaagctt ataagcaaca gaat                                              24

<210> SEQ ID NO 18
<211> LENGTH: 42
<212> TYPE: DNA
<213> ORGANISM: Artificial sequence
<220> FEATURE:
<223> OTHER INFORMATION: Synthesized polynucleotide

<400> SEQUENCE: 18
gcttatagga gcggcataat tcagggagcc cagaagctgg ta                          42

<210> SEQ ID NO 19
<211> LENGTH: 15
<212> TYPE: DNA
<213> ORGANISM: Artificial sequence
<220> FEATURE:
<223> OTHER INFORMATION: Synthesized polynucleotide

<400> SEQUENCE: 19
cctagacacg acact                                                        15

<210> SEQ ID NO 20
<211> LENGTH: 18
<212> TYPE: DNA
<213> ORGANISM: Artificial sequence
<220> FEATURE:
<223> OTHER INFORMATION: Synthesized polynucleotide

<400> SEQUENCE: 20
ttttatgaaa agatgcag                                                     18

<210> SEQ ID NO 21
<211> LENGTH: 45
<212> TYPE: DNA
<213> ORGANISM: Artificial sequence
<220> FEATURE:
<223> OTHER INFORMATION: Synthesized polynucleotide

<400> SEQUENCE: 21
gccagcagct cagacaggga actattattc tacaatgagc agttc                       45

<210> SEQ ID NO 22
<211> LENGTH: 278
<212> TYPE: PRT
<213> ORGANISM: Artificial sequence
<220> FEATURE:
<223> OTHER INFORMATION: Synthesized polypeptide

<400> SEQUENCE: 22

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60
```

```
Met Ile Leu Val Ile Arg Gln Glu Ala Tyr Lys Gln Gln Asn Ala Thr
 65                  70                  75                  80

Glu Asn Arg Phe Ser Val Asn Phe Gln Lys Ala Ala Lys Ser Phe Ser
                 85                  90                  95

Leu Lys Ile Ser Asp Ser Gln Leu Gly Asp Ala Ala Met Tyr Phe Cys
            100                 105                 110

Ala Tyr Arg Ser Gly Ile Ile Gln Gly Ala Gln Lys Leu Val Phe Gly
        115                 120                 125

Gln Gly Thr Arg Leu Thr Ile Asn Pro Asn Ile Gln Asn Pro Asp Pro
130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
        195                 200                 205

Ala Cys Ala Asn Ala Phe Asn Asn Ser Ile Ile Pro Glu Asp Thr Phe
    210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser
            275
```

<210> SEQ ID NO 23
<211> LENGTH: 837
<212> TYPE: DNA
<213> ORGANISM: Artificial sequence
<220> FEATURE:
<223> OTHER INFORMATION: Synthesized polynucleotide

<400> SEQUENCE: 23

```
atggcatgcc ctggcttcct gtgggcactt gtgatctcca cctgtcttga atttagcatg      60
gctcagacag tcactcagtc tcaaccagag atgtctgtgc aggaggcaga gaccgtgacc     120
ctgagctgca catatgacac cagtgagagt gattattatt tattctggta caagcagcct     180
cccagcaggc agatgattct cgttattcgc caagaagctt ataagcaaca gaatgcaaca     240
gagaatcgtt tctctgtgaa cttccagaaa gcagccaaat ccttcagtct caagatctca     300
gactcacagc tgggggatgc cgcgatgtat ttctgtgctt ataggagcgg cataattcag     360
ggagcccaga gctggtatt tggccaagga accaggctga ctatcaaccc aaatatccag     420
aaccctgacc ctgccgtgta ccagctgaga gactctaaat ccagtgacaa gtctgtctgc     480
ctattcaccg attttgattc tcaaacaaat gtgtcacaaa gtaaggattc tgatgtgtat     540
atcacagaca aaactgtgct agacatgagg tctatggact caagagcaa cagtgctgtg     600 gcctggagca acaaatctga ctttgcatgt gcaaacgcct caacaacag cattattcca     660 gaagacacct tcttccccag cccagaaagt tcctgtgatg tcaagctggt cgagaaaagc     720
tttgaaacag atacgaacct aaactttcaa aacctgtcag tgattgggtt ccgaatcctc     780
```
ctcctgaaag tggccgggtt taatctgctc atgacgctgc ggctgtggtc cagctaa    837

<210> SEQ ID NO 24
<211> LENGTH: 324
<212> TYPE: PRT
<213> ORGANISM: Artificial sequence
<220> FEATURE:
<223> OTHER INFORMATION: Synthesized polypeptide

<400> SEQUENCE: 24

Met Leu Ser Pro Asp Leu Pro Asp Ser Ala Trp Asn Thr Arg Leu Leu
1               5                   10                  15

Cys Arg Val Met Leu Cys Leu Leu Gly Ala Gly Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Ser Asp Arg Glu Leu
        115                 120                 125

Leu Phe Tyr Asn Glu Gln Phe Phe Gly Pro Gly Thr Arg Leu Thr Val
    130                 135                 140

Leu Glu Asp Leu Lys Asn Val Phe Pro Pro Glu Val Ala Val Phe Glu
145                 150                 155                 160

Pro Ser Glu Ala Glu Ile Ser His Thr Gln Lys Ala Thr Leu Val Cys
                165                 170                 175

Leu Ala Thr Gly Phe Tyr Pro Asp His Val Glu Leu Ser Trp Trp Val
            180                 185                 190

Asn Gly Lys Glu Val His Ser Gly Val Ser Thr Asp Pro Gln Pro Leu
        195                 200                 205

Lys Glu Gln Pro Ala Leu Asn Asp Ser Arg Tyr Cys Leu Ser Ser Arg
    210                 215                 220

Leu Arg Val Ser Ala Thr Phe Trp Gln Asn Pro Arg Asn His Phe Arg
225                 230                 235                 240

Cys Gln Val Gln Phe Tyr Gly Leu Ser Glu Asn Asp Glu Trp Thr Gln
                245                 250                 255

Asp Arg Ala Lys Pro Val Thr Gln Ile Val Ser Ala Glu Ala Trp Gly
            260                 265                 270

Arg Ala Asp Cys Gly Phe Thr Ser Glu Ser Tyr Gln Gln Gly Val Leu
        275                 280                 285

Ser Ala Thr Ile Leu Tyr Glu Ile Leu Leu Gly Lys Ala Thr Leu Tyr
    290                 295                 300

Ala Val Leu Val Ser Ala Leu Val Leu Met Ala Met Val Lys Arg Lys
305                 310                 315                 320

Asp Ser Arg Gly

<210> SEQ ID NO 25
<211> LENGTH: 975
<212> TYPE: DNA
<213> ORGANISM: Artificial sequence
<220> FEATURE:
<223> OTHER INFORMATION: Synthesized polynucleotide

<400> SEQUENCE: 25

```
atgcttagtc ctgacctgcc tgactctgcc tggaacacca ggctcctctg ccgtgtcatg      60
ctttgtctcc tgggagcagg ttcagtggct gctggagtca tccagtcccc aagacatctg     120
atcaaagaaa agagggaaac agccactctg aaatgctatc ctatccctag acacgacact     180
gtctactggt accagcaggg tccaggtcag gacccccagt tcctcatttc gttttatgaa     240
aagatgcaga gcgataaagg aagcatccct gatcgattct cagctcaaca gttcagtgac     300
tatcattctg aactgaacat gagctccttg gagctggggg actcagccct gtacttctgt     360
gccagcagct cagacaggga actattattc tacaatgagc agttcttcgg ccagggaca      420
cggctcaccg tgctagagga cctgaaaaac gtgttccac cgaggtcgc tgtgtttgag       480
ccatcagaag cagagatctc ccacacccaa aaggccacac tggtgtgcct ggccacaggc     540
ttctaccccg accacgtgga gctgagctgg tgggtgaatg gaaggaggt gcacagtggg      600
gtcagcacag acccgcagcc cctcaaggag cagcccgccc tcaatgactc agatactgc      660
ctgagcagcc gcctgagggt ctcggccacc ttctggcaga accccgcaa ccacttccgc      720
tgtcaagtcc agttctacgg gctctcggag aatgacgagt ggacccagga tagggccaaa     780
cctgtcaccc agatcgtcag cgccgaggcc tggggtagag cagactgtgg cttcacctcc     840
gagtcttacc agcaagggt cctgtctgcc accatcctct atgagatctt gctagggaag     900
gccaccttgt atgccgtgct ggtcagtgcc ctcgtgctga tggccatggt caagagaaag     960
gattccagag gctaa                                                      975
```

<210> SEQ ID NO 26
<211> LENGTH: 212
<212> TYPE: PRT
<213> ORGANISM: Artificial sequence
<220> FEATURE:
<223> OTHER INFORMATION: Synthesized polypeptide

<400> SEQUENCE: 26

```
Met Ala Gln Thr Val Thr Gln Ser Gln Pro Glu Met Ser Val Gln Glu
1               5                   10                  15

Ala Glu Thr Val Thr Leu Ser Cys Thr Tyr Asp Thr Ser Glu Ser Asp
            20                  25                  30

Tyr Tyr Leu Phe Trp Tyr Lys Gln Pro Pro Ser Arg Gln Met Ile Leu
        35                  40                  45

Val Ile Arg Gln Glu Ala Tyr Lys Gln Gln Asn Ala Thr Glu Asn Arg
    50                  55                  60

Phe Ser Val Asn Phe Gln Lys Ala Ala Lys Ser Phe Ser Leu Lys Ile
65                  70                  75                  80

Ser Asp Ser Gln Leu Gly Asp Ala Ala Met Tyr Phe Cys Ala Tyr Arg
                85                  90                  95

Ser Gly Ile Ile Gln Gly Ala Gln Lys Leu Val Phe Gly Gln Gly Thr
            100                 105                 110

Arg Leu Thr Ile Asn Pro Asn Ile Gln Asn Pro Asp Pro Ala Val Tyr
        115                 120                 125

Gln Leu Arg Asp Ser Lys Ser Ser Asp Lys Ser Val Cys Leu Phe Thr
    130                 135                 140

Asp Phe Asp Ser Gln Thr Asn Val Ser Gln Ser Lys Asp Ser Asp Val
145                 150                 155                 160
```

```
Tyr Ile Thr Asp Lys Cys Val Leu Asp Met Arg Ser Met Asp Phe Lys
            165                 170                 175

Ser Asn Ser Ala Val Ala Trp Ser Asn Lys Ser Asp Phe Ala Cys Ala
        180                 185                 190

Asn Ala Phe Asn Asn Ser Ile Ile Pro Glu Asp Thr Phe Phe Pro Ser
        195                 200                 205

Pro Glu Ser Ser
    210
```

<210> SEQ ID NO 27
<211> LENGTH: 636
<212> TYPE: DNA
<213> ORGANISM: Artificial sequence
<220> FEATURE:
<223> OTHER INFORMATION: Synthesized polynucleotide

<400> SEQUENCE: 27

```
atggcgcaga ccgtgaccca gtctcaacca gagatgtctg tgcaggaggc agagaccgtg    60
accctgagct gcacatatga caccagtgag agtgattatt atttattctg gtacaagcag   120
cctcccagca ggcagatgat tctcgttatt cgccaagaag cttataagca acagaatgca   180
acagagaatc gtttctctgt gaacttccag aaagcagcca atccttcag tctcaagatc    240 tcagactcac agctggggga tgccgcgatg tatttctgtg cttataggag cggcataatt   300
cagggagccc agaagctggt atttggccaa ggaaccaggc tgactatcaa cccaaatatc   360
cagaaccctg accctgccgt gtaccagctg agagactcta gtcgagtgaa caagtctgtc   420
tgcctattca ccgattttga ttctcaaaca atgtgtcac aaagtaagga ttctgatgtg    480
tatatcacag acaaatgtgt gctagacatg aggtctatgg acttcaagag caacagtgct   540
gtggcctgga gcaacaaatc tgactttgca tgtgcaaacg ccttcaacaa cagcattatt   600
ccagaagaca ccttcttccc cagcccagaa agttcc                              636
```

<210> SEQ ID NO 28
<211> LENGTH: 247
<212> TYPE: PRT
<213> ORGANISM: Artificial sequence
<220> FEATURE:
<223> OTHER INFORMATION: Synthesized polypeptide

<400> SEQUENCE: 28

```
Met Ala Ala Gly Val Ile Gln Ser Pro Arg His Leu Ile Lys Glu Lys
1               5                   10                  15

Arg Glu Thr Ala Thr Leu Lys Cys Tyr Pro Ile Pro Arg His Asp Thr
            20                  25                  30

Val Tyr Trp Tyr Gln Gln Gly Pro Gly Gln Asp Pro Gln Phe Leu Ile
        35                  40                  45

Ser Phe Tyr Glu Lys Met Gln Ser Asp Lys Gly Ser Ile Pro Asp Arg
    50                  55                  60

Phe Ser Ala Gln Gln Phe Ser Asp Tyr His Ser Glu Leu Asn Met Ser
65                  70                  75                  80

Ser Leu Glu Leu Gly Asp Ser Ala Leu Tyr Phe Cys Ala Ser Ser Ser
                85                  90                  95

Asp Arg Glu Leu Leu Phe Tyr Asn Glu Gln Phe Phe Gly Pro Gly Thr
            100                 105                 110

Arg Leu Thr Val Leu Glu Asp Leu Lys Asn Val Phe Pro Pro Glu Val
        115                 120                 125

Ala Val Phe Glu Pro Ser Glu Ala Glu Ile Ser His Thr Gln Lys Ala
```

```
                130              135                 140
Thr Leu Val Cys Leu Ala Thr Gly Phe Tyr Pro Asp His Val Glu Leu
145                 150                 155                 160

Ser Trp Trp Val Asn Gly Lys Glu Val His Ser Gly Val Cys Thr Asp
                165                 170                 175

Pro Gln Pro Leu Lys Glu Gln Pro Ala Leu Asn Asp Ser Arg Tyr Ala
                180                 185                 190

Leu Ser Ser Arg Leu Arg Val Ser Ala Thr Phe Trp Gln Asp Pro Arg
                195                 200                 205

Asn His Phe Arg Cys Gln Val Gln Phe Tyr Gly Leu Ser Glu Asn Asp
                210                 215                 220

Glu Trp Thr Gln Asp Arg Ala Lys Pro Val Thr Gln Ile Val Ser Ala
225                 230                 235                 240

Glu Ala Trp Gly Arg Ala Asp
                245

<210> SEQ ID NO 29
<211> LENGTH: 741
<212> TYPE: DNA
<213> ORGANISM: Artificial sequence
<220> FEATURE:
<223> OTHER INFORMATION: Synthesized polynucleotide

<400> SEQUENCE: 29
atggcggcgg gcgtgattca gtccccaaga catctgatca agaaaagag ggaaacagcc      60 actctgaaat gctatcctat ccctagacac gacactgtct actggtacca gcagggtcca    120
ggtcaggacc cccagttcct catttcgttt tatgaaaaga tgcagagcga taaggaagc    180 atccctgatc gattctcagc tcaacagttc agtgactatc attctgaact gaacatgagc    240
tccttggagc tgggggactc agccctgtac ttctgtgcca gcagctcaga cagggaacta    300
ttattctaca atgagcagtt cttcgggcca gggacacggc tcaccgtgct agaggacctg    360
aaaaacgtgt tcccacccga ggtcgctgtg tttgagccat cagaagcaga gatctcccac    420
acccaaaagg ccacactggt gtgcctggcc accggtttct accccgacca cgtggagctg    480
agctggtggg tgaatgggaa ggaggtgcac agtgggtct gcacagaccc gcagcccctc    540
aaggagcagc ccgccctcaa tgactccaga tacgctctga gcagccgcct gagggtctcg    600
gccaccttct ggcaggaccc ccgcaaccac ttccgctgtc aagtccagtt ctacgggctc    660
tcggagaatg acgagtggac ccaggatagg gccaaacccg tcacccagat cgtcagcgcc    720
gaggcctggg gtagagcaga c                                              741

<210> SEQ ID NO 30
<211> LENGTH: 258
<212> TYPE: PRT
<213> ORGANISM: Artificial sequence
<220> FEATURE:
<223> OTHER INFORMATION: Synthesized polypeptide

<400> SEQUENCE: 30

Met Ala Gln Thr Val Thr Gln Ser Gln Pro Glu Leu Ser Val Gln Glu
1               5                   10                  15

Gly Glu Thr Val Thr Ile Ser Cys Thr Tyr Asp Thr Ser Glu Ser Asp
                20                  25                  30

Tyr Tyr Leu Phe Trp Tyr Lys Gln Pro Pro Ser Arg Gln Pro Ile Leu
            35                  40                  45

Val Ile Arg Gln Glu Ala Tyr Lys Gln Gln Asn Ala Thr Glu Asn Arg
```

```
                   50                  55                  60
Phe Ser Val Asn Phe Gln Lys Ala Ala Lys Ser Phe Ser Leu Lys Ile
 65                  70                  75                  80

Ser Asp Val Gln Pro Gly Asp Ala Ala Met Tyr Phe Cys Ala Tyr Arg
                     85                  90                  95

Ser Gly Ile Ile Gln Ala Gln Lys Leu Val Phe Gly Gln Gly Thr
                100                 105                 110

Arg Leu Thr Ile Asn Pro Gly Gly Ser Glu Gly Gly Ser Glu
            115                 120                 125

Gly Gly Gly Ser Glu Gly Gly Ser Glu Gly Gly Thr Gly Ala Ala
        130                 135                 140

Gly Val Thr Gln Ser Pro Arg His Leu Ser Val Glu Lys Gly Glu Thr
145                 150                 155                 160

Val Thr Leu Lys Cys Tyr Pro Ile Pro Arg His Asp Thr Val Tyr Trp
                165                 170                 175

Tyr Gln Gln Gly Pro Gly Gln Asp Leu Gln Phe Leu Ile Ser Phe Tyr
                180                 185                 190

Glu Lys Met Gln Ser Asp Lys Gly Ser Ile Pro Asp Arg Phe Ser Ala
                195                 200                 205

Gln Gln Phe Ser Asp Tyr His Ser Glu Leu Asn Ile Ser Ser Val Glu
                210                 215                 220

Pro Gly Asp Ser Ala Leu Tyr Phe Cys Ala Ser Ser Asp Arg Glu
225                 230                 235                 240

Leu Leu Phe Tyr Asn Glu Gln Phe Phe Gly Pro Gly Thr Arg Leu Thr
                245                 250                 255

Val Asp

<210> SEQ ID NO 31
<211> LENGTH: 774
<212> TYPE: DNA
<213> ORGANISM: Artificial sequence
<220> FEATURE:
<223> OTHER INFORMATION: Synthesized polynucleotide

<400> SEQUENCE: 31
atggctcaaa ctgttactca gagccaaccg gagctgagcg tgcaagaggg tgaaaccgtt        60
accatcagct gcacctacga caccagcgaa agcgattact acctgttctg gtataagcag       120
ccgccgagcc gtcaaccgat cctggttatt cgtcaggaag cgtacaaaca gcaaaacgcg       180
accgaaaacc gtttcagcgt gaactttcag aaggcggcga aaagcttcag cctgaagatc       240
agcgacgttc aaccgggcga tgcggcgatg tactttgcg cgtatcgtag cggtatcatt       300
cagggcgcgc aaaaactggt gttcggtcag ggcacccgtc tgaccattaa cccgggtggc       360
ggtagcgagg gcggtggcag cgaaggtggc ggtagcgagg gcggtggcag cgaaggtggc       420
accggtgcgg cgggcgtgac ccaaagcccg cgtcacctga gcgtggagaa gggtgaaacc       480
gttaccctga atgctatcc gatcccgcgt cacgacaccg tttactggta tcagcaaggt       540
ccgggccagg atctgcaatt cctgatcagc ttttacgaga agatgcagag cgacaaaggt       600
agcattccgg atcgtttcag cgcgcagcaa tttagcgact atcacagcga gctgaacatt       660
agcagcgtgg aaccgggtga cagcgcgctg tacttctgcg cgagcagcag cgatcgtgag       720
ctgctgtttt ataacgaaca gttctttggt ccgggcaccc gtctgaccgt tgat            774

<210> SEQ ID NO 32
<211> LENGTH: 118
```

```
<212> TYPE: PRT
<213> ORGANISM: Artificial sequence
<220> FEATURE:
<223> OTHER INFORMATION: Synthesized polypeptide

<400> SEQUENCE: 32

Met Ala Gln Thr Val Thr Gln Ser Gln Pro Glu Leu Ser Val Gln Glu
1               5                   10                  15

Gly Glu Thr Val Thr Ile Ser Cys Thr Tyr Asp Thr Ser Glu Ser Asp
                20                  25                  30

Tyr Tyr Leu Phe Trp Tyr Lys Gln Pro Pro Ser Arg Gln Pro Ile Leu
            35                  40                  45

Val Ile Arg Gln Glu Ala Tyr Lys Gln Gln Asn Ala Thr Glu Asn Arg
    50                  55                  60

Phe Ser Val Asn Phe Gln Lys Ala Ala Lys Ser Phe Ser Leu Lys Ile
65                  70                  75                  80

Ser Asp Val Gln Pro Gly Asp Ala Ala Met Tyr Phe Cys Ala Tyr Arg
                85                  90                  95

Ser Gly Ile Ile Gln Gly Ala Gln Lys Leu Val Phe Gly Gln Gly Thr
            100                 105                 110

Arg Leu Thr Ile Asn Pro
        115

<210> SEQ ID NO 33
<211> LENGTH: 354
<212> TYPE: DNA
<213> ORGANISM: Artificial sequence
<220> FEATURE:
<223> OTHER INFORMATION: Synthesized polynucleotide

<400> SEQUENCE: 33
atggctcaaa ctgttactca gagccaaccg gagctgagcg tgcaagaggg tgaaaccgtt    60
accatcagct gcacctacga caccagcgaa agcgattact acctgttctg gtataagcag   120
ccgccgagcc gtcaaccgat cctggttatt cgtcaggaag cgtacaaaca gcaaaacgcg   180
accgaaaacc gtttcagcgt gaactttcag aaggcggcga aaagcttcag cctgaagatc   240
agcgacgttc aaccgggcga tgcggcgatg tactttttgcg cgtatcgtag cggtatcatt   300
cagggcgcgc aaaaactggt gttcggtcag ggcacccgtc tgaccattaa cccg          354

<210> SEQ ID NO 34
<211> LENGTH: 116
<212> TYPE: PRT
<213> ORGANISM: Artificial sequence
<220> FEATURE:
<223> OTHER INFORMATION: Synthesized polypeptide

<400> SEQUENCE: 34

Ala Ala Gly Val Thr Gln Ser Pro Arg His Leu Ser Val Glu Lys Gly
1               5                   10                  15

Glu Thr Val Thr Leu Lys Cys Tyr Pro Ile Pro Arg His Asp Thr Val
                20                  25                  30

Tyr Trp Tyr Gln Gln Gly Pro Gly Gln Asp Leu Gln Phe Leu Ile Ser
            35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Ile Ser Ser
65                  70                  75                  80

Val Glu Pro Gly Asp Ser Ala Leu Tyr Phe Cys Ala Ser Ser Ser Asp
```

-continued

```
                85                  90                  95

Arg Glu Leu Leu Phe Tyr Asn Glu Gln Phe Phe Gly Pro Gly Thr Arg
            100                 105                 110

Leu Thr Val Asp
        115

<210> SEQ ID NO 35
<211> LENGTH: 348
<212> TYPE: DNA
<213> ORGANISM: Artificial sequence
<220> FEATURE:
<223> OTHER INFORMATION: Synthesized polynucleotide

<400> SEQUENCE: 35
gcggcgggcg tgacccaaag cccgcgtcac ctgagcgtgg agaagggtga aaccgttacc      60
ctgaaatgct atccgatccc gcgtcacgac accgtttact ggtatcagca aggtccgggc     120
caggatctgc aattcctgat cagcttttac gagaagatgc agagcgacaa aggtagcatt     180
ccggatcgtt tcagcgcgca gcaatttagc gactatcaca gcgagctgaa cattagcagc     240
gtggaaccgg gtgacagcgc gctgtacttc tgcgcgagca gcagcgatcg tgagctgctg     300
ttttataacg aacagttctt tggtccgggc acccgtctga ccgttgat                  348

<210> SEQ ID NO 36
<211> LENGTH: 24
<212> TYPE: PRT
<213> ORGANISM: Artificial sequence
<220> FEATURE:
<223> OTHER INFORMATION: Synthesized polypeptide

<400> SEQUENCE: 36

Gly Gly Gly Ser Glu Gly Gly Gly Ser Glu Gly Gly Gly Ser Glu Gly
1               5                   10                  15

Gly Gly Ser Glu Gly Gly Thr Gly
            20

<210> SEQ ID NO 37
<211> LENGTH: 72
<212> TYPE: DNA
<213> ORGANISM: Artificial sequence
<220> FEATURE:
<223> OTHER INFORMATION: Synthesized polynucleotide

<400> SEQUENCE: 37
ggtggcggta gcgagggcgg tggcagcgaa ggtggcggta gcgagggcgg tggcagcgaa      60
ggtggcaccg gt                                                          72
```

T-CELL RECEPTOR RECOGNIZING SSX2 ANTIGEN

TECHNICAL FIELD

The present invention relates to TCRs capable of recognizing short peptides derived from SSX2 antigens. The present invention also relates to SSX2-specific T cells obtained by transducing the above-mentioned TCRs, and uses thereof in the prevention and treatment of SSX2-related diseases.

BACKGROUND

SSX2 is the X breakpoint of synovial sarcoma, also known as HOM-MEL-40. SSX2 is one of ten highly homologous nucleic acid proteins in the SSX family. SSX protein is a tumor antigen in testis, which is only expressed in tumor cells and testicular embryo cells without MHC expression. SSX2 is expressed in various human cancer cells, including but not limited to liver cancer, lung cancer, fibrosarcoma, breast cancer, colon cancer, and prostate cancer. KASEKIFYV (SEQ ID NO: 9) is a short peptide derived from SSX2 antigen and is a target for treating SSX2-related diseases. For the treatment of the above diseases, chemotherapy and radiotherapy can be used, which however will cause damage to normal cells.

T cell adoptive immunotherapy is to transfer reactive T cells specific to target cell antigens into a patient's body so that they can act against the target cells. T cell receptor (TCR) is a membrane protein on the surface of T cells that can recognize antigen short peptides on the surface of corresponding target cells. In the immune system, the combination of antigen short peptide-specific TCR and short peptide-major histocompatibility complex (pMHC complex) will induce the direct physical contact between T cells and antigen presenting cells (APC), and then other cell membrane surface molecules of T cells and APC interact with each other, causing a series of subsequent cell signaling and other physiological reactions, so that T cells with different antigen specificities can exert immune effects on target cells thereof. Therefore, a skilled person are dedicated to isolating TCRs specific to SSX2 antigen short peptides, and transducing the TCR to T cells to obtain T cells specific to SSX2 antigen short peptides, so that they can play a role in cellular immunotherapy.

SUMMARY OF THE INVENTION

The purpose of the present invention is to provide a T cell receptor that recognizes short peptides of SSX2 antigen.

In the first aspect of the present invention, a T cell receptor (TCR) that can bind to the KASEKIFYV-HLA A0201 complex is provided.

In another preferred embodiment, the TCR comprises a TCR α chain variable domain and a TCR β chain variable domain, and the amino acid sequence of CDR3 of the TCR α chain variable domain is AYRSGIIQGAQKLV (SEQ ID NO: 12); and/or the the amino acid sequence of CDR3 of the TCR β chain variable domain is ASSSDRELLFYNEQF (SEQ ID NO: 15).

In another preferred embodiment, 3 complementarity determining regions (CDR) of the TCR α chain variable domain are:

α CDR1-
TSESDYY (SEQ ID NO: 10)

α CDR2-
QEAYKQQN (SEQ ID NO: 11)

α CDR3-
AYRSGIIQGAQKLV; (SEQ ID NO: 12)

and/or
3 complementarity determining regions of the TCR β chain variable domain are:

β CDR1-
PRHDT (SEQ ID NO: 13)

β CDR2-
FYEKMQ (SEQ ID NO: 14)

β CDR3-
ASSSDRELLFYNEQF. (SEQ ID NO: 15)

In another preferred embodiment, the TCR comprises a TCR α chain variable domain and a TCR β chain variable domain, and the TCR α chain variable domain is an amino acid sequence having at least 90% sequence identity with SEQ ID NO: 1; and/or the TCR β chain variable domain is an amino acid sequence with at least 90% sequence identity with SEQ ID NO: 5.

In another preferred embodiment, the TCR comprises a TCR α chain variable domain, the amino acid sequence of which is SEQ ID NO: 1.

In another preferred embodiment, the TCR comprises a TCR β chain variable domain, the amino acid sequence of which is SEQ ID NO: 5.

In another preferred embodiment, the TCR is a αβ heterodimer, which comprises a TCR α chain constant region TRAC*01 and a TCR β chain constant region TRBC1*01 or TRBC2*01.

In another preferred embodiment, the amino acid sequence of the TCR α chain is SEQ ID NO: 3 and/or the amino acid sequence of the TCR β chain is SEQ ID NO: 7.

In another preferred embodiment, the TCR is soluble.

In another preferred embodiment, the TCR is a single-chain TCR.

In another preferred embodiment, the TCR is formed by connecting the α chain variable domain and the β chain variable domain through a peptide linking sequence.

In another preferred embodiment, the TCR has one or more mutations at amino acid position 11, 13, 19, 21, 53, 76, 89, 91, or 94 of the α chain variable region, and/or at the last 3, 5 or 7 amino acid position of the short peptide of the α chain J gene; and/or the TCR has one or more mutations at amino acid position 11, 13, 19, 21, 53, 76, 89, 91, or 94 of the β chain variable region, and/or at the last 2, 4, or 6 amino acid position of the short peptide of the β chain J gene, wherein the amino acid position number is based on the position number listed in IMGT (International Immunogenetics Information System).

In another preferred embodiment, the amino acid sequence of the α chain variable domain of the TCR comprises SEQ ID NO: 32 and/or the amino acid sequence of the β chain variable domain of the TCR comprises SEQ ID NO: 34.

In another preferred embodiment, the amino acid sequence of the TCR is SEQ ID NO: 30.

In another preferred embodiment, the TCR comprises (a) all or part of the TCR α chain except for its transmembrane domain, and (b) all or part of the TCR β chain except for its transmembrane domain;

and each of (a) and (b) comprise the functional variable domain, or the functional variable domain and at least a portion of the constant domain of the TCR chain, respectively.

In another preferred embodiment, cysteine residues form an artificial disulfide bond between the α and β chain constant domains of the TCR.

In another preferred embodiment, the cysteine residues forming the artificial interchain disulfide bond in the TCR are substituted for one or more groups of amino acids selected from the following:

Thr48 of TRAC*01 exon 1 and Ser57 of TRBC1*01 or TRBC2*01 exon 1;

Thr45 of TRAC*01 exon 1 and Ser77 of TRBC1*01 or TRBC2*01 exon 1;

Tyr10 of TRAC*01 exon 1 and Ser17 of TRBC1*01 or TRBC2*01 exon 1;

Thr45 of TRAC*01 exon 1 and Asp59 of TRBC1*01 or TRBC2*01 exon 1;

Ser15 of TRAC*01 exon 1 and Glu15 of TRBC1*01 or TRBC2*01 exon 1;

Arg53 of TRAC*01 exon 1 and Ser54 of TRBC1*01 or TRBC2*01 exon 1;

Pro89 of TRAC*01 exon 1 and Ala19 of TRBC1*01 or TRBC2*01 exon 1; and

Tyr10 of TRAC*01 exon 1 and Glu20 of TRBC1*01 or TRBC2*01 exon 1.

In another preferred embodiment, the amino acid sequence of the TCR α chain is SEQ ID NO: 26 and/or the amino acid sequence of the TCR β chain is SEQ ID NO: 28.

In another preferred embodiment, an artificial interchain disulfide bond is contained between α chain variable region and β chain constant region of the TCR.

In another preferred embodiment, cysteine residues forming the artificial interchain disulfide bond in the TCR are substituted for one or more groups of amino acids selected from the following:

amino acid at position 46 of TRAV and amino acid at position 60 of TRBC1*01 or TRBC2*01 exon 1;

amino acid at position 47 of TRAV and amino acid at position 61 of TRBC1*01 or TRBC2*01 exon 1;

amino acid at position 46 of TRAV and amino acid at position 61 of TRBC1*01 or TRBC2*01 exon 1; or amino acid at position 47 of TRAV and amino acid at position 60 of TRBC1*01 or TRBC2*01 exon 1.

In another preferred embodiment, the TCR comprises α chain variable domain and β chain variable domain as well as all or part of β chain constant domains except for its transmembrane domain, however it does not comprise α chain constant domain, and a chain variable domain and β chain of the TCR form a heterodimer.

In another preferred embodiment, a conjugate binds to the α chain and/or β chain of the TCR at C- or N-terminal.

In another preferred embodiment, the conjugate that binds to the TCR is a detectable label, a therapeutic agent, a PK modified moiety, or a combination thereof. Preferably, the therapeutic agent is an anti-CD3 antibody.

In the second aspect of the invention, a multivalent TCR complex is provided, wherein the multivalent TCR complex comprises at least two TCR molecules, and at least one TCR molecule is the TCR of the first aspect of the invention.

In the third aspect of the invention, a nucleic acid molecule is provided, comprising a nucleic acid sequence encoding the TCR molecule of the first aspect of the invention, or a complement sequence thereof.

In another preferred embodiment, the nucleic acid molecule comprises the nucleotide sequence SEQ ID NO: 2 or SEQ ID NO: 33 encoding the variable domain of the TCR α chain.

In another preferred embodiment, the nucleic acid molecule comprises the nucleotide sequence SEQ ID NO: 6 or SEQ ID NO: 35 encoding the variable domain of the TCR β chain.

In another preferred embodiment, the nucleic acid molecule comprises the nucleotide sequence SEQ ID NO: 4 encoding the TCR α chain and/or the nucleotide sequence SEQ ID NO: 8 encoding the variable domain of the TCR β chain.

In the fourth aspect of the invention, a vector is provided, comprising the nucleic acid molecule of the third aspect of the invention; preferably, the vector is a viral vector; and more preferably, the vector is a lentiviral vector.

In the fifth aspect of the present invention, an isolated host cell is provided, comprising the vector of the fourth aspect of the present invention or having the exogenous nucleic acid molecule of the third aspect of the present invention integrated into its genome.

In the sixth aspect of the invention, a cell is provided, which is transduced with the nucleic acid molecule of the third aspect of the present invention or the vector of the fourth aspect of the invention; and preferably, the cell is a T cell or stem cell.

In the seventh aspect of the invention, a pharmaceutical composition is provided, comprising a pharmaceutically acceptable carrier, and the TCR of the first aspect of the invention, or the TCR complex of the second aspect of the invention, the nucleic acid molecule of the third aspect of the present invention, the vector of the fourth aspect of the invention, or the cell of the sixth aspect of the invention.

In the eighth aspect of the invention, use of the TCR of the first aspect of the invention, or the TCR complex of the second aspect of the invention, the nucleic acid molecule of the third aspect of the present invention, the vector of the fourth aspect of the invention, or the cell of the sixth aspect of the invention is provided for preparing a medicament for treating tumor or autoimmune disease.

In an ninth aspect of the present invention, a method for treating a disease is provided, comprising administering an appropriate amount of the TCR of the first aspect of the present invention, the TCR complex of the second aspect of the present invention, the nucleic acid molecule of the third aspect of the present invention, the vector of the fourth aspect of the invention, the cell of the sixth aspect of the invention, or the pharmaceutical composition of the seventh aspect of the invention to a subject in need thereof;

Preferably, the disease is a tumor, and preferably, the tumor is Hepatocellular carcinoma.

It is to be understood that within the scope of the present invention, the various technical features of the present invention and the technical features specifically described hereinafter (as in the embodiments) may be combined with each other to constitute a new or preferred technical solution, which will not be repeated herein one by one.

DESCRIPTION OF DRAWINGS

FIG. 1a, FIG. 1b, FIG. 1c, FIG. 1d, FIG. 1e and Figure if are the amino acid sequence of the TCR α chain variable domain, the nucleotide sequence of the TCR α chain variable domain, the amino acid sequence of the TCR α chain, the nucleotide sequence of the TCR α chain, the amino acid sequence of the TCR α chain with the leader sequence and the nucleotide sequence of the TCR α chain with the leader sequence.

FIG. 2a, FIG. 2b, FIG. 2c, FIG. 2d, FIG. 2e and FIG. 2f are the amino acid sequence of the TCR β chain variable domain, the nucleotide sequence of the TCR β chain variable domain, the amino acid sequence of the TCR β chain, the nucleotide sequence of the TCR β chain, the amino acid sequence of the TCR β chain with the leader sequence and the nucleotide sequence of the TCR β chain with the leader sequence.

FIG. 3 shows the CD8+ and tetramer-PE double positive staining results of monoclonal cells.

FIG. 4a and FIG. 4b are the amino acid sequence and nucleotide sequence of the soluble TCR α chain, respectively.

FIG. 5a and FIG. 5b are the amino acid sequence and nucleotide sequence of the soluble TCR β chain, respectively.

FIG. 6 is a gel image of soluble TCR obtained after purification. The leftmost lane is the molecular weight marker, and the 3 lanes on the right are the non-reducing gel.

FIG. 7a and FIG. 7b are the amino acid sequence and nucleotide sequence of the single-chain TCR, respectively.

FIG. 8a and FIG. 8b are the amino acid sequence and nucleotide sequence of the variable domain of the single-chain TCR α chain, respectively.

FIG. 9a and FIG. 9b are the amino acid sequence and nucleotide sequence of the variable domain of the single-chain TCR β chain, respectively.

FIG. 10a and FIG. 10b are the amino acid sequence and nucleotide sequence of the linker of the single-chain TCR, respectively.

FIG. 11 is a gel image of soluble single-chain TCR obtained after purification. The right lane is the molecular weight marker (marker), and the left lane is the non-reducing gel.

MODES FOR CARRYING OUT THE INVENTION

Figure 12:
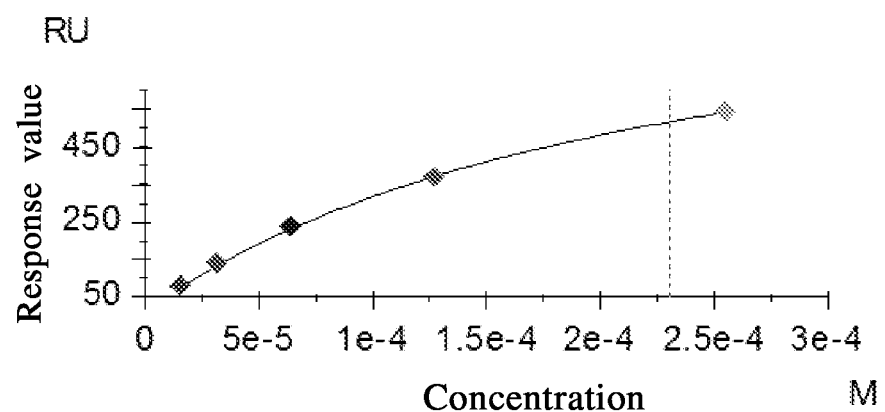
FIG. 12 is a BIAcore kinetic map of the binding of the soluble TCR of the present invention to KASEKIFYV-HLA A0201 complex.

After extensive and in-depth research, the inventors found a TCR that can specifically bind to the SSX2 antigen short peptide KASEKIFYV (SEQ ID NO: 9). The antigen short peptide KASEKIFYV (SEQ ID NO: 9) can form a complex with HLA A0201 and be presented together to the cell surface. The present invention also provides a nucleic acid molecule encoding the TCR and a vector containing the nucleic acid molecule. In addition, the present invention also provides cells transduced with the TCR of the present invention.

Term

MHC molecules are proteins of the immunoglobulin superfamily, and can be MHC molecules of class I or class II. Therefore, it is specific for the presentation of antigens. Different individuals have different MHCs and can present different short peptides in a protein antigen to the surface of respective APC cells thereof. Human MHC is usually called HLA gene or HLA complex.

T cell receptor (TCR) is the only receptor for presenting specific peptide antigens in Major Histocompatibility Complex (MHC). The exogenous or endogenous peptides may be the only sign of abnormality in a cell. In the immune system, direct physical contact of a T-cell and an antigen presenting cell (APC) will be initiated by the binding of antigen-specific TCRs to pMHC complexes. Then, the interaction of other membrane molecules in T cell and APC occurs and the subsequent cell signaling and other physiological responses are initiated so that a range of different antigen-specific T cells exert immune effects on their target cells.

TCR is a glycoprotein on the surface of the cell membrane existing as a heterodimer of α chain/β chain or γ chain/δ chain. In 95% of T cells, TCR heterodimers consist of α and β chains, while 5% of T cells have TCRs consisting of γ and δ chains. Natural αβ heterodimeric TCR has α chain and β chain, and a chain and β chain constitute subunits of αβ heterodimeric TCR. Generally speaking, each of α and β chains includes a variable region, a connecting region and a constant region. The β chain usually also comprises a short variable region between the variable region and the connecting region, but the variable region is often regarded as a part of the connecting region. Each variable region comprises 3 CDRs (complementarity determining regions), CDR1, CDR2, and CDR3 embedded in framework regions. The CDR regions determine the binding of TCR to pMHC complex, wherein CDR3 is formed from recombination of the variable region and the connecting region, and called the hypervariable region. The α and β chains of a TCR are generally regarded as having two "domains" respectively, namely a variable domain and a constant domain. The variable domain consists of a connected variable region and a connecting region. The sequence of the constant domain of a TCR can be found in the public database of the International Immunogenetics Information System (IMGT). For example, the sequence of the constant domain of the α chain of a TCR molecule is "TRAC*01", and the sequence of the constant domain of the β chain of a TCR molecule is "TRBC1*01" or "TRBC2*01". In addition, the α and β chains of a TCR also comprise transmembrane region and cytoplasmic region, which are very short.

In the present invention, the terms "polypeptide of the present invention", "TCR of the present invention", and "T cell receptor of the present invention" are used interchangeably.

Natural Inter-Chain Disulfide Bond and Artificial Inter-Chain Disulfide Bond

A group of disulfide bonds is present between the Cα and Cβ chains in the membrane proximal region of a native TCR, which is named herein as "natural inter-chain disulfide bond". In the present invention, an inter-chain covalent disulfide bond which is artificially introduced and the position of which is different from the position of a natural inter-chain disulfide bond is named as "artificial inter-chain disulfide bond".

For conveniently describing the position of disulfide bond, in the present invention, the positions of the amino acid sequences of TRAC*01 and TRBC1*01 or TRBC2*01 are sequentially numbered in order from N-terminal to C-terminal. For example, the 60$^{th}$ amino acid in the order from N-terminal to C-terminal in TRBC1*01 or TRBC2*01 is P (valine), which can be described as Pro60 of TRBC1*01 or TRBC2*01 in the present invention, and can also be expressed as the amino acid at position 60 of TRBC1*01 or TRBC2*01 exon 1. For another example, the 61$^{st}$ amino acid in the order from N-terminal to C-terminal in TRBC1*01 or TRBC2*01 is Q (glutamine), which can be described as Gln61 of TRBC1*01 or TRBC2*01 exon 1 in the invention, and can also be expressed as the amino acid at position 61 of TRBC1*01 or TRBC2*01 exon 1, and so on. In the present invention, the positions of the amino acid sequences of variable regions TRAV and TRBV are numbered according to the positions listed in IMGT. As for an amino acid in TRAV, the position is numbered as 46 in IMGT, which is described in the present invention as the amino acid at position 46 of TRAV, and so on. In the present invention, if the sequence positions of other amino acids are specifically described, the special description shall prevail.

DETAILED DESCRIPTION OF THE INVENTION

TCR Molecule

In the process of antigen processing, the antigen is degraded inside the cell and then carried to the cell surface by MHC molecules. T cell receptors can recognize peptide-MHC complexes on the surface of antigen-presenting cells. Therefore, in the first aspect of the present invention, a TCR molecule capable of binding to the KASEKIFYV-HLA A0201 complex is provided. Preferably, the TCR molecule is isolated or purified. Each of the α and β chains of the TCR has three complementarity determining regions (CDR).

In a preferred embodiment of the present invention, the α chain of the TCR includes CDRs having the following amino acid sequences:

α CDR1-
TSESDYY                                 (SEQ ID NO: 10)

α CDR2-
QEAYKQQN                                (SEQ ID NO: 11)

α CDR3-
AYRSGIIQGAQKLV;                         (SEQ ID NO: 12)

and/or 3 complementarity determining regions of the TCR β chain variable domain are:

β CDR1-
PRHDT                                   (SEQ ID NO: 13)

β CDR2-
FYEKMQ                                  (SEQ ID NO: 14)

β CDR3-
ASSSDRELLFYNEQF.                        (SEQ ID NO: 15)

The above amino acid sequences of the CDR regions of the present invention can be embedded into any suitable framework structure to prepare a chimeric TCR. As long as the framework structure is compatible with the CDR regions of the TCR of the present invention, a skilled person can design or synthesize TCR molecules with corresponding functions based on the CDR regions disclosed in the present invention. Therefore, the TCR molecule of the present invention refers to a TCR molecule comprising the above-mentioned α and/or β chain CDR region sequences and any suitable framework structure. The TCR α chain variable domain of the present invention is an amino acid sequence having at least 90%, preferably 95%, and more preferably 98% sequence identity with SEQ ID NO: 1; and/or the TCR β chain variable domain of the present invention is an amino acid sequence having at least 90%, preferably 95%, more preferably 98% sequence identity with SEQ ID NO: 5.

In a preferred embodiment of the present invention, the TCR molecule of the present invention is a heterodimer consisting of α and β chains. Specifically, the α chain of the heterodimeric TCR molecule, on the one hand, comprises a variable domain and a constant domain, and the amino acid sequence of the α chain variable domain comprises CDR1 (SEQ ID NO: 10) and CDR2 (SEQ ID NO: 11) and CDR3 (SEQ ID NO: 12) of the above α chain. Preferably, the TCR molecule comprises a α chain variable domain amino acid sequence SEQ ID NO: 1. More preferably, the amino acid sequence of the α chain variable domain of the TCR molecule is SEQ ID NO: 1. On the other hand, the β chain of the heterodimeric TCR molecule comprises a variable domain and a constant domain, and the amino acid sequence of the β chain variable domain comprises CDR1 (SEQ ID NO: 13) and CDR2 (SEQ ID NO: 14) and CDR3 (SEQ ID NO: 15). Preferably, the TCR molecule comprises the β chain variable domain amino acid sequence SEQ ID NO: 5. More preferably, the amino acid sequence of the β chain variable domain of the TCR molecule is SEQ ID NO: 5.

In a preferred embodiment of the present invention, the TCR molecule of the present invention is a single-chain TCR molecule consisting of part or all of the α chain and/or part or all of the β chain. Description of single-chain TCR molecules can be found in Chung et al (1994) Proc. Natl. Acad. Sci. USA 91, 12654-12658. According to the literature, a skilled person can easily construct single-chain TCR molecules containing the CDRs of the present invention. Specifically, the single-chain TCR molecule comprises Vα, Vβ and Cβ, and is preferably connected in an order from N-terminal to C-terminal.

The amino acid sequence of the α chain variable domain of the single-chain TCR molecule comprises CDR1 (SEQ ID NO: 10) and CDR2 (SEQ ID NO: 11) and CDR3 (SEQ ID NO: 12) of the above α chain. Preferably, the single-chain TCR molecule comprises a α chain variable domain amino acid sequence SEQ ID NO: 1. More preferably, the amino acid sequence of the α chain variable domain of the single-chain TCR molecule is SEQ ID NO: 1. The amino acid sequence of the β chain variable domain of the single-chain TCR molecule comprises CDR1 (SEQ ID NO: 13) and CDR2 (SEQ ID NO: 14) and CDR3 (SEQ ID NO: 15). Preferably, the single-chain TCR molecule comprises the β chain variable domain amino acid sequence SEQ ID NO: 5. More preferably, the amino acid sequence of the β chain variable domain of the single-chain TCR molecule is SEQ ID NO: 5.

In a preferred embodiment of the present invention, the constant domain of the TCR molecule of the present invention is a human constant domain. A skilled person know or can obtain the amino acid sequence of the human constant domain by referring to relevant books or public databases of IMGT (International Immunogenetics Information System). For example, the constant domain sequence of the α chain of the TCR molecule of the present invention can be "TRAC*01", and the constant domain sequence of the β chain of the TCR molecule can be "TRBC1*01" or "TRBC2*01". The amino acid at 53$^{rd}$ position of the amino acid sequence given in TRAC*01 of IMGT is Arg, which is represented herein as: Arg53 of TRAC*01 exon 1, and so on. Preferably, the amino acid sequence of the α chain of the TCR molecule of the present invention is SEQ ID NO: 3, and/or the amino acid sequence of the 13 chain is SEQ ID NO: 7.

The naturally occurring TCR is a membrane protein that is stabilized by its transmembrane domain. Just as immunoglobulins (antibodies) which can be used as antigen recognition molecules, TCRs can also be developed for diagnosis and treatment, and it is necessary to obtain soluble TCR molecules. The soluble TCR molecule does not comprise its transmembrane region. The soluble TCR has a wide range of uses, which can be used not only to study the interaction between TCR and pMHC, but also as a diagnostic tool for detecting infections or as a marker for autoimmune diseases. Similarly, the soluble TCR can be used to deliver therapeutic agents (such as cytotoxic compounds or immunostimulatory compounds) to cells presenting specific antigens. In addition, the soluble TCR can also be combined with other molecules (such as anti-CD3 antibodies) to redirect T cells to target cells that present specific antigens. A soluble TCR specific to the SSX2 antigen short peptide is also obtained in to invention.

For obtaining a soluble TCR, the TCR of the present invention, on the one hand, may be a TCR in which an artificial disulfide bond is introduced between the residues of its α and β chain constant domains. Cysteine residues form an artificial interchain disulfide bond between the α and β chain constant domains of the TCR. Cysteine residues can be substituted for other amino acid residues at appropriate positions in the natural TCR to form an artificial interchain disulfide bond. For example, cysteine residues replacing Thr48 of TRAC*01 exon 1 and replacing Ser57 of TRBC1*01 or TRBC2*01 exon 1 form a disulfide bond. Other sites for introducing cysteine residues to form disulfide bonds can also be: Thr45 of TRAC*01 exon 1 and Ser77 of TRBC1*01 or TRBC2*01 exon 1; Tyr10 of TRAC*01 exon 1 and Ser17 of TRBC1*01 or TRBC2*01 exon 1; Thr45 of TRAC*01 exon 1 and Asp59 of TRBC1*01 or TRBC2*01 exon 1; Ser15 of TRAC*01 exon 1 and Glu15 of TRBC1*01 or TRBC2*01 exon 1; Arg53 of TRAC*01 exon 1 and Ser54 of TRBC1*01 or TRBC2*01 exon 1; Pro89 of TRAC*01 exon 1 and Ala19 of TRBC1*01 or TRBC2*01 exon 1; or Tyr10 of TRAC*01 exon 1 and Glu20 of TRBC1*01 or TRBC2*01 exon 1. That is, cysteine residues replace any set of positions in the constant domains of the α and β chains. A maximum of 50, or a maximum of 30, or a maximum of 15, or a maximum of 10, or a maximum of 8 or less amino acids can be truncated at one or more C-termini of the TCR constant domain of the present invention, so that it does not include Cysteine residues to achieve the purpose of deleting natural disulfide bonds, and the cysteine residues forming natural disulfide bonds can be mutated to another amino acid to achieve the above purpose.

As described above, the TCR of the present invention may comprise an artificial disulfide bond introduced between the residues of the constant domains of its α and β chains. It should be noted that, the TCR of the present invention can comprise the TRAC constant domain sequence and the TRBC1 or TRBC2 constant domain sequence regardless of whether the constant domains comprise the introduced artificial disulfide bonds as said above. The TRAC constant domain sequence and the TRBC1 or TRBC2 constant domain sequence of the TCR can be linked by natural disulfide bonds present in the TCR.

For obtaining a soluble TCR, the TCR of the present invention, on the other hand, also includes a TCR having mutations in its hydrophobic core region. These mutations in the hydrophobic core region are preferably mutations that can improve the stability of the soluble TCR of the present invention, as described in WO2014/206304. Such TCR can have a mutation in the following positions of hydrophobic core of the variable domains: amino acid position 11, 13, 19, 21, 53, 76, 89, 91, or 94 of the variable region (α and/or β chain), and/or the last 3, 5 or 7 amino acid position of the α chain J gene (TRAJ), and/or the last 2, 4, or 6 amino acid position of the 13 chain J gene (TRBJ), wherein the amino acid position number is based on the position number listed in IMGT (International Immunogenetics Information System). A skilled person can know the above-mentioned international immunogenetics information system, and can obtain the position numbers of the amino acid residues of different TCRs in IMGT according to the database.

In the present invention, the TCR in which the hydrophobic core region is mutated may be a stable soluble single-chain TCR consisting of the variable domains of the α and β chains of a TCR connected by a flexible peptide chain. It should be noted that the flexible peptide chain in the present invention can be any peptide chain suitable for connecting the variable domains of TCR α and β chains. For example, in the single-chain soluble TCR constructed in Example 4 of the present invention, the α chain variable domain amino acid sequence is SEQ ID NO: 32, and the encoding nucleotide sequence is SEQ ID NO: 33; β chain variable domain amino acid sequence is SEQ ID NO:34, and the encoding nucleotide sequence is SEQ ID NO:35.

In addition, in terms of stability, CN 201510260322.4 also disclosed that the introduction of an artificial interchain disulfide bond between the α chain variable region and the β chain constant region of the TCR can significantly improve the stability of the TCR. Therefore, the high-affinity TCR of the present invention may also comprise an artificial interchain disulfide bond between the α chain variable region and the β chain constant region. Specifically, cysteine residues forming an artificial interchain disulfide bond between the α chain variable region and the β chain constant region of the TCR are substituted for: amino acid at position 46 of TRAV and amino acid at position 60 of TRBC1*01 or TRBC2*01 exon 1; amino acid at position 47 of TRAV and amino acid at position 61 of TRBC1*01 or TRBC2*01 exon 1; amino acid at position 46 of TRAV and amino acid at position 61 of TRBC1*01 or TRBC2*01 exon 1; or amino acid at position 47 of TRAV and amino acid at position 60 of TRBC1*01 or TRBC2*01 exon 1. Preferably, such TCR may comprise (i) all or part of TCR α chain except for its transmembrane domain, and (ii) all or part of TCR β chain except for its transmembrane domain, wherein both of (i) and (ii) comprise the variable domain and at least a portion of constant domains of the TCR chain, and the α chain and β chain form a heterodimer. More preferably, such TCR may comprise α chain variable domain and β chain variable domain and all or part of β chain constant domain except for the transmembrane domain, which, however, does not comprise α chain constant domain, and the α chain variable domain of the TCR and the β chain form a heterodimer.

The TCR of the present invention can be provided in a form of multivalent complex. The multivalent TCR complex of the present invention comprises a polymer formed by combining two, three, four or more TCRs of the present invention, for example, a tetrameric domain of p53 can be used to produce a tetramer. Alternatively, more TCRs of the invention can be combined with another molecule to form a complex. The TCR complexes of the invention can be used to track or target cells that present a particular antigen in vitro or in vivo, or produce intermediates of other multivalent TCR complexes with such uses.

The TCR of the present invention may be used alone or combined with a conjugate in a covalent manner or other manner, preferably in a covalent manner. The conjugate includes a detectable label (for diagnostic purposes, wherein the TCR is used to detect the presence of a cell presenting KASEKIFYV-HLA A0201 complex), a therapeutic agent, a PK (protein kinase) modifying moiety, or combination of any of the above described substances.

Detectable labels for diagnostic purposes include, but are not limited to, fluorescent or luminescent labels, radioactive labels, MRI (magnetic resonance imaging) or CT (electron computed tomography) contrast agents, or enzymes capable of producing detectable products.

Therapeutic agents that can be combined with or coupled to the TCRs of the invention include, but are not limited to: 1. Radionuclides (Koppe et al., 2005, Cancer metastasis reviews 24, 539); 2. Biotoxin (Chaudhary et al., 1989, Nature 339, 394; Epel et al., 2002, Cancer Immunology and Immunotherapy 51, 565); 3. Cytokines, such as IL-2, etc. (Gillies et al., 1992, National Academy of Sciences (PNAS) 89, 1428; Card et al., 2004, Cancer Immunology and Immunotherapy 53, 345; Halin et al., 2003, Cancer Research 63, 3202); 4. Antibody Fc fragment (Mosquera et al., 2005, The Journal Of Immunology 174, 4381); 5. Antibody scFv fragments (Zhu et al., 1995, International Journal of Cancer 62, 319); 6. Gold nanoparticles/Nanorods (Lapotko et al., 2005, Cancer letters 239, 36; Huang et al., 2006, Journal of the American Chemical Society 128, 2115); 7. Viral particles (Peng et al., 2004, Gene therapy 11, 1234); 8. Liposomes (Mamot et al., 2005, Cancer research 65, 11631); 9. Nanomagnetic particles; 10. Prodrug activating enzymes (e.g., DT-diaphorase (DTD) or biphenyl hydrolase-like protein (BPHL); 11. chemotherapeutic agent (e.g., cisplatin) or any form of nanoparticles, and the like.

In addition, the TCR of the present invention may also be a hybrid TCR containing sequences derived from more than one species. For example, studies have shown that, compared wuth human TCR, murine TCR can be expressed more effectively in human T cells. Therefore, the TCR of the present invention may comprise a human variable domain and a murine constant domain. The disadvantage of this method is that an immune response may be triggered. Therefore, when used in adoptive T cell therapy, there should be a regulatory scheme for immunosuppression to allow the implantation of T cells expressing murine.

It should be understood that the names of amino acids herein are represented by the internationally accepted single English letter or three English letters, and the correspondence between the single English letter and the three English letter of the names of amino acid is as follows: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), Val (V).

Nucleic Acid Molecule

In the second aspect of the present invention, a nucleic acid molecule encoding the TCR molecule of the first aspect of the present invention or a part thereof is provided, and the part may be one or more CDRs, variable domains of α and/or β chains, and α chains and/or β chain.

The nucleotide sequence encoding the α chain CDR region of the TCR molecule of the first aspect of the present invention is as follows:

α CDR1-
(SEQ ID NO: 16)
accagtgagagtgattattat

α CDR2-
(SEQ ID NO: 17)
caagaagcttataagcaacagaat

α CDR3-
(SEQ ID NO: 18)
gcttataggagcggcataattcagggagcccagaagctggta

The nucleotide sequence encoding the β chain CDR region of the TCR molecule of the first aspect of the present invention is as follows:

β CDR1-
(SEQ ID NO: 19)
cctagacacgacact

β CDR2-
(SEQ ID NO: 20)
ttttatgaaaagatgcag

β CDR3-
(SEQ ID NO: 21)
gccagcagctcagacagggaactattattctacaatgagcagttc

Therefore, the nucleotide sequence of the nucleic acid molecule of the present invention encoding the TCR α chain of the present invention includes SEQ ID NO: 16, SEQ ID NO: 17 and SEQ ID NO: 18, and/or the nucleotide sequence of the nucleic acid molecule of the present invention encoding the TCR β chain of the present invention includes SEQ ID NO: 19, SEQ ID NO: 20, and SEQ ID NO: 21.

The nucleotide sequence of the nucleic acid molecule of the present invention may be of single-chain or double-chain, and the nucleic acid molecule may be RNA or DNA, and may or may not comprise introns. Preferably, the nucleotide sequence of the nucleic acid molecule of the present invention does not comprise introns but can encode the polypeptide of the present invention. For example, the nucleotide sequence of the nucleic acid molecule of the present invention encoding the variable domain of the TCR α chain of the present invention includes SEQ ID NO: 2 and/or the nucleotide sequence of the nucleic acid molecule of the present invention encoding the variable domain of the TCR β chain of the present invention includes SEQ ID NO: 6. Alternatively, the nucleotide sequence of the nucleic acid molecule of the present invention encoding the variable domain of the TCR α chain of the present invention includes SEQ ID NO: 33 and/or the nucleotide sequence of the nucleic acid molecule of the present invention encoding the variable domain of the TCR β chain of the present invention includes SEQ ID NO: 35. More preferably, the nucleotide sequence of the nucleic acid molecule of the present invention comprises SEQ ID NO: 4 and/or SEQ ID NO: 8. Alternatively, the nucleotide sequence of the nucleic acid molecule of the present invention is SEQ ID NO: 31.

It should be understood that different nucleotide sequences can encode the same polypeptide due to the degeneracy of the genetic code. Therefore, a nucleic acid sequence encoding the TCR of the invention may be the same as the nucleic acid sequence set forth in the Figures of the invention or a degenerate variant thereof. By way of one example herein, "degenerate variant" refers to a nucleic acid sequence which encodes a protein with a sequence of SEQ ID NO: 1, but is differences from the sequence of SEQ ID NO: 2.

The nucleotide sequence can be codon-optimized. Different cells are different in the use of specific codons. The codons in a sequence can be changed to increase the expression according to the cell type. Codon usage tables for mammalian cells and many other organisms are well known to a skilled person.

The full-length sequence of the nucleic acid molecule of the present invention or fragments thereof can usually be obtained by but not limited to PCR amplification method, recombination method or artificial synthesis method. At present, the DNA sequence encoding the TCR (or a fragment or derivative thereof) of the present invention can be obtained completely through chemical synthesis. This DNA sequence can then be introduced into various existing DNA molecules (or such as vectors) and cells known in the art. DNA can be a coding strand or a non-coding strand.

Vector

The invention also relates to vectors comprising the nucleic acid molecules of the invention, including expression vectors, that is, constructs that can be expressed in vivo or in vitro. Commonly used vectors include bacterial plasmids, bacteriophages, and animal and plant viruses.

Viral delivery systems include but are not limited to adenovirus vectors, adeno-associated virus (AAV) vectors, herpes virus vectors, retrovirus vectors, lentivirus vectors, and baculovirus vectors.

Preferably, the vector can transfer the nucleotide of the present invention into a cell, such as a T cell, so that the cell expresses a TCR specific for the SSX2 antigen. Ideally, the vector should be able to continuously express at a high level in T cells.

Cells

The invention also relates to host cells genetically engineered using the vectors or coding sequences of the invention. The host cell comprises the vector of the present invention or has the nucleic acid molecule of the present invention integrated into the chromosome. The host cell is selected from: prokaryotic cells and eukaryotic cells, such as *E. coli*, yeast cells, CHO cells and the like.

In addition, the invention also encompasses isolated cells, particularly T cells, expressing the TCR of the invention. The T cells may be derived from T cells isolated from a subject, or may be a mixed cell population isolated from a subject, such as a part of a peripheral blood lymphocyte (PBL) population. For example, the cells can be isolated from peripheral blood mononuclear cells (PBMC), and can be CD4+ helper T cells or CD8+ cytotoxic T cells. The cells can be in a mixed population of CD4+ helper T cells/CD8+ cytotoxic T cells. Generally, the cells can be activated with antibodies (e.g., anti-CD3 or anti-CD28 antibodies), so that they can be more easily transfected with, for example a vector containing a nucleotide sequence encoding the TCR molecule of the present invention.

Alternatively, the cells of the present invention can also be or derived from stem cells, such as hematopoietic stem cells (HSC). Transferring a gene to HSC won't result in the expression of TCR on the cell surface, since CD3 molecules are not expressed on the surface of stem cells. However, when stem cells differentiate into lymphoid precursors that migrate to the thymus, the expression of CD3 molecules will initiate the expression of the introduced TCR molecules on the surface of thymocytes.

There are a number of methods suitable for T cell transfection with DNA or RNA encoding TCR of the invention (e.g., Robbins et al., (2008) J. Immunol. 180: 6116-6131). T cells expressing the TCR of the invention can be used in adoptive immunotherapy. A skilled person can know many suitable methods for performing adoptive therapy (e.g., Rosenberg et al., (2008) Nat Rev Cancer 8(4): 299-308).

SSX2 Antigen-Related Disease

The present invention also relates to a method for treating and/or preventing SSX2-related diseases in a subject, including a step of adoptive transferring SSX2-specific T cells to the subject. The SSX2-specific T cells can recognize the KASEKIFYV-HLA A0201 complex.

The SSX2-specific T cells of the present invention can be used to treat any SSX2-related diseases that present the SSX2 antigen short peptide KASEKIFYV-HLA A0201 complex, including but not limited to tumors, such as liver cancer, lung cancer, fibrosarcoma, breast cancer, colon cancer, prostate cancer.

Treatment Method

Treatment can be carried out by isolating T cells from patients or volunteers suffering from AFP antigen-related diseases, introducing the TCR of the present invention into the above T cells, and then infusing the genetically engineered cells back into the patient. Therefore, the present invention provides a method for the treatment of AFP-related diseases, including infusing the isolated T cell expressing the TCR of the present invention into a patient, and preferably, the T cell is derived from the patient himself. Generally, the method includes (1) isolating T cells from a patient, (2) in vitro transducing the T cells with the nucleic acid molecule of the present invention or a nucleic acid molecule capable of encoding TCR molecules of the present invention, and (3) infusing genetically engineered T cells into patients in vivo. The number of cells to be isolated, transfected and reinfused can be determined by a physician.

Main advantages of the present invention:

(1) The TCR of the present invention can bind to the SSX2 antigen short peptide complex KASEKIFYV-HLA A0201, and the cells transduced with the TCR of the present invention can be specifically activated.

The invention is further illustrated by the following specific examples. It is to be understood that these examples are for illustrative purposes only and are not intended to limit the scope of the invention. The experimental methods in the following examples which do not specify the specific conditions are usually performed under conventional conditions, for example, conditions described in Sambrook and Russell et al., Molecular Cloning-A Laboratory Manual (Third Edition) (2001) CSHL Publishing company, or in accordance with the conditions recommended by the manufacturer. Percentages and parts are by weight unless otherwise stated.

Example 1. Cloning of SSX2 Antigen Short Peptide Specific T Cells

The synthetic short peptide KASEKIFYV (SEQ ID NO.: 9; Beijing Cypress Gene Technology Co., Ltd.) was used to stimulate peripheral blood lymphocytes (PBL) from healthy volunteers with genotype HLA-A0201. The KASEKIFYV (SEQ ID NO: 9) short peptide was refolded with biotin-labeled HLA-A0201 to prepare pHLA haploid. These haploids were combined with PE-labeled streptavidin (BD Company) to form PE-labeled tetramers, and the tetramers and anti-CD8-APC double-positive cells were sorted. The sorted cells were amplified and the secondary sorting was performed according to the above method, and then the limiting dilution method was performed for monoclone.

Monoclonal cells were stained with tetramers, and the screened double positive clones are shown in FIG. 3.

The function and specificity of the T cell clone were further tested by ELISPOT experiment. A skilled person is familiar with the method of using ELISPOT assay to detect cell function. The effector cells used in the IFN-γELISPOT experiment of this example are the T cell clones obtained in the present invention, the target cells are T2 cells loaded with the short peptides of the present invention, and the control group are T2 cells loaded with other short peptides and T2 cells without any short peptide.

Figure 14:
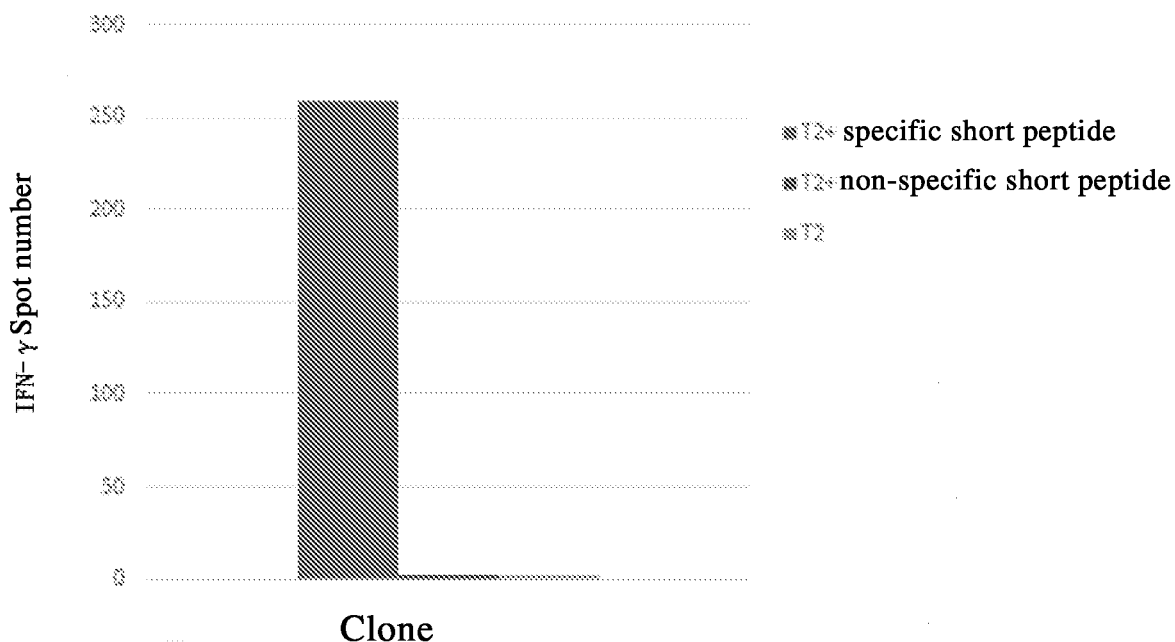
FIG. 14 shows the result of the ELISPOT activation function verification of the obtained T cell clone.

Firstly, a ELISPOT plate was prepared. The procedure of the ELISPOT experiment is as follows: the components to be tested were added to the ELISPOT plate in the following order: 40 µl T2 cells 5×10$^5$ cells/ml (i.e., 20,000 T2 cells/well), 40 µl effector cells (2000 T cell clones/well), the experimental group was added with 20 µl of specific short peptide, the control group was added with 20 µl of non-specific short peptide, the blank group was added with 20 µl of medium (test medium), and duplicate wells were set. And then the plate was incubated overnight (37° C., 5% CO2). Then the plate was washed and subjected to secondary detection and color development. The plate was dried for 1 hour, and then the spots formed on the membrane were counted with an immunospot plate reader (ELISPOT READER system; AID company). The experimental results are shown in FIG. 14. The obtained specific antigen-specific T cell clones have specific responses to T2 cells loaded with short peptides of the present invention, but basically no response to T2 cells loaded with other irrelevant peptides and T2 cells loaded not loaded with short peptides.

Example 2. Obtaining TCR Gene of T Cell Clone Specific for Short Peptide of SSX2 Antigen and Constructing Vector Quick-RNA™ MiniPrep (ZYMO research) was used to extract the total RNA of the antigen short peptide KASEKI-FYV(SEQ ID NO: 9)-specific and HLA-A0201-restricted T cell clones selected in Example 1. SMART RACE cDNA amplification kit (clontech) was used to synthesize the cDNA, and the used primers were designed in the C-terminal conserved region of the human TCR gene. The sequence was cloned into a T vector (TAKARA) for sequencing. It should be noted that this sequence is a complementary sequence and does not contain introns. After sequencing, the sequence structures of the α chain and β chain of the TCR expressed by the double-positive clone are shown in FIG. 1 and FIG. 2, respectively. FIG. 1a, FIG. 1b, FIG. 1c, FIG. 1d, FIG. 1e and Figure if are the TCR α chain variable domain amino acid sequence, TCR α chain variable domain nucleotide sequence, TCR α chain amino acid sequence, TCR α chain nucleotide sequence, the TCR α chain amino acid sequence with a leader sequence and the TCR α chain nucleotide sequence with the leader sequence; and FIG. 2a, FIG. 2b, FIG. 2c, FIG. 2d, FIG. 2e and FIG. 2f are the TCR β chain variable domain amino acid sequence, TCR β chain variable domain nucleotide sequence, TCR β chain amino acid sequence, TCR β chain nucleotide sequence, the TCR β chain amino acid sequence with a leader sequence and the TCR β chain nucleotide sequence with the leader sequence.

It was identified that the α chain comprises CDRs with the following amino acid sequences:

α CDR1-
TSESDYY                                              (SEQ ID NO: 10)

α CDR2-
QEAYKQQN                                             (SEQ ID NO: 11)

α CDR3-
AYRSGIIQGAQKLV                                       (SEQ ID NO: 12)

and the β chain comprises CDRs with the following amino acid sequences:

β CDR1-
PRHDT                                                (SEQ ID NO: 13)

β CDR2-
FYEKMQ                                               (SEQ ID NO: 14)

β CDR3-
ASSSDRELLFYNEQF.                                     (SEQ ID NO: 15)

The full-length genes of TCR α chain and β chain were cloned into lentiviral expression vector pLenti (addgene) by overlapping PCR. Specifically, the full-length genes of TCR α chain and TCR β chain were connected by overlap PCR to obtain TCRα-2A-TCRβ fragment. The lentiviral expression vector and TCRα-2A-TCRβ were digested and connected to obtain the pLenti-TRA-2A-TRB-IRES-NGFR plasmid. As a control, a lentiviral vector pLenti-eGFP expressing eGFP was also constructed. Then 293T/17 was used to package pseudovirus.

Example 3. Expression, Refolding and Purification of Soluble TCR Specific for SSX2 Antigen Short Peptide For obtaining a soluble TCR molecule, the α and β chains of the TCR molecule of the present invention may only contain the variable domain and part of the constant domain, respectively, and a cysteine residue was introduced into the constant domains of the α and β chains to form an artificial interchain disulfide bond. The positions for introducing cysteine residues were Thr48 of TRAC*01 exon 1 and Ser57 of TRBC1*01 or TRBC2*01 exon 1, respectively; the amino acid sequence and nucleotide sequence of the α chain were shown in FIG. 4a and FIG. 4b, respectively, and the amino acid sequence and nucleotide sequence of the β chain were shown in FIG. 5a and FIG. 5b, respectively. The target gene sequences of the above-mentioned TCR α and β chains were synthesized and inserted into an expression vector pET28a+ (Novagene) according to the method described in "Molecular Cloning a Laboratory Manual" (3$^{rd}$ version, Sambrook and Russell), the upstream and downstream cloning sites were NcoI and NotI respectively. The inserted fragment was confirmed by sequencing.

The expression vectors for TCR α and β chains were transformed into bacteria BL21 (DE3) by chemical transformation, and the bacteria were grown in LB medium, and induced with a final concentration of 0.5 mM IPTG at OD$_{600}$=0.6. After TCR α and β chains were expressed, the formed inclusion bodies were extracted with BugBuster Mix (Novagene) and repeatedly washed with BugBuster solution. The inclusion bodies were finally dissolved in 6 M guanidine hydrochloride, 10 mM dithiothreitol (DTT), 10 mM ethylenediamine acetic acid (EDTA), 20 mM Tris (pH 8.1).

The dissolved TCR α and β chains were quickly mixed in 5 M urea, 0.4 M arginine, 20 mM Tris (pH 8.1), 3.7 mM cystamine, 6.6 mM β-mercapoethylamine (4° C.) at a mass ratio of 1:1, with a final concentration of 60 mg/mL. After mixing, the solution was subjected to dialysis against 10 times volume of deionized water (4° C.). After 12 hours, the deionized water was changed to a buffer (20 mM Tris, pH 8.0) and the dialysis was conducted at 4° C. for another 12 hours. After dialysis, the solution was filtered through a 0.45 μM filter membrane and purified through an anion exchange column (HiTrap Q HP, 5 ml, GE Healthcare). The eluted peak contained the successfully renatured α and β dimers of TCR, which was confirmed by SDS-PAGE. The TCR was then further purified through gel filtration chromatography (HiPrep 16/60, Sephacryl S-100 HR, GE Healthcare). The purity of the purified TCR was determined by SDS-PAGE to be greater than 90%, and the concentration thereof was determined by the BCA method. The SDS-PAGE gel image of the soluble TCR obtained in the present invention is shown in FIG. 6.

Example 4. Generation of Soluble Single-Chain TCR Specific for SSX2 Antigen Short Peptide A method of site-directed mutagenesis was used according to WO2014/206304 to construct a stable single-chain TCR molecule consisting of TCR α and β chain variable domains of Example 2 connected by a flexible short peptide (linker). The amino acid sequence and nucleotide sequence of the single-chain TCR molecule are shown in FIGS. 7a and 7b, respectively. The amino acid sequence and nucleotide sequence of the α chain variable domain are shown in FIG. 8a and FIG. 8b respectively; the amino acid sequence and nucleotide sequence of the β chain variable domain are shown in FIG. 9a and FIG. 9b respectively; the amino acid sequence and nucleotide sequence of the linker are shown in FIG. 10a and FIG. 10b, respectively.

The target gene was digested with NcoI and NotI, and ligated with pET28a vector digested with NcoI and NotI. The ligation product was transformed into *E. coli* DH5α, plated on a kanamycin-containing LB plate, inverted and cultured at 37° C. overnight, and the positive clones were picked for PCR screening. Positive recombinants were sequenced to determine the correct sequence and the recombinant plasmid was extracted and transferred into *E. coli* BL21 (DE3) for expression.

Example 5. Expression, Refolding and Purification of Soluble Single-Chain TCR Specific for SSX2 Antigen Short Peptide All of BL21(DE 3) colonies containing the recombinant plasmid pET28a-template chain prepared in Example 4 were inoculated into LB medium containing kanamycin, and cultured at 37° C. until OD600 was 0.6-0.8. IPTG was added to a final concentration of 0.5 mM, and cultured at 37° C. for another 4 hrs. The cell pellets were harvested by centrifugation at 5000 rpm for 15 mins, and the cell pellets were lysed with Bugbuster Master Mix (Merck). The inclusion bodies were recovered by centrifugation at 6000 rpm for 15 min, followed by washing with Bugbuster (Merck) to remove cell debris and membrane fraction. The inclusion bodies were collected by centrifugation at 6000 rpm for 15 min, and dissolved in a buffer (20 mM Tris-HCl pH 8.0, 8 M urea), and the insoluble matters were removed by high-speed centrifugation. The supernatant was quantitativly determined by BCA method, and then dispensed and stored at −80° C. until use.

To 5 mg of dissolved single-chain TCR inclusion body protein, 2.5 mL of buffer (6 M Gua-HCl, 50 mM Tris-HCl pH 8.1, 100 mM NaCl, 10 mM EDTA) was added, then DTT was added to a final concentration of 10 mM, and incubated at 37° C. for 30 min. The single-chain TCRs as treated above was added dropwise to a 125 mL of refolding buffer (100 mM Tris-HCl pH 8.1, 0.4 M L-arginine, 5 M urea, 2 mM EDTA, 6.5 mM β-mercapthoethylamine, 1.87 mM Cystamine) with a syringe, and stirred at 4° C. for 10 min. Then the refolded solution was loaded into a cellulose membrane dialysis bag with a cut-off of 4 kDa, and the dialysis bag was placed in 1 L of pre-cooled water, and stirred slowly at 4° C. overnight. After 17 hours, the dialysis liquid was changed to 1 L of pre-chilled buffer (20 mM Tris-HCl pH 8.0) and dialysis was continued for 8 h at 4° C. The dialysis liquid was then replaced with the same fresh buffer and dialysis was continued overnight. After 17 hours, the sample was filtered through a 0.45 μm filter, vacuum degassed and purified through an anion exchange column (HiTrap Q HP, GE Healthcare) with a linear gradient elution of 0-1 M NaCl prepared with 20 mM Tris-HCl pH 8.0. The collected fractions were subjected to SDS-PAGE analysis, and the fractions containing single-chain TCRs were concentrated and further purified by a gel filtration column (Superdex 75 10/300, GE Healthcare), and the target components were also subjected to SDS-PAGE analysis.

The eluted fractions for BIAcore analysis was further tested for purity using gel filtration. The conditions were as follows: chromatographic column Agilent Bio SEC-3 (300 A, φ 7.8×300 mm), mobile phase 150 mM phosphate buffer, flow rate 0.5 mL/min, column temperature 25° C., and UV detection wavelength 214 nm.

The SDS-PAGE gel image of the soluble single-chain TCR obtained in the present invention is shown in FIG. 11.

Example 6. Binding Characterization

BIAcore Analysis

This example proves that the soluble TCR molecule of the present invention can specifically bind to the KASEKIFYV-HLA A0201 complex.

The binding activity of the TCR molecule obtained in Example 3 and Example 5 to KASEKIFYV-HLA A0201 complex was detected using BIAcore T200 real-time analysis system. The anti-streptavidin antibody (GenScript) was added to a coupling buffer (10 mM sodium acetate buffer, pH 4.77), and then the antibody was passed through a CM5 chip pre-activated with EDC and NHS to immobilize the antibody on the surface of the chip. The unreacted activated surface was finally blocked with a solution of ethanolamine in hydrochloric acid to complete the coupling process at a coupling level of about 15,000 RU.

A low concentration of streptavidin flowed over the surface of the antibody-coated chip, then KASEKIFYV-HLA A0201 complex flowed through the detection channel with another channel being used as a reference channel. 0.05 mM biotin flowed over the chip for 2 min at a flow rate of 10 μL/min, thereby blocking the remaining binding sites for streptavidin.

The preparation process for the above KASEKIFYV-HLA A0201 complex is described as follows:

a. Purification 100 ml of *E. coli* liquid induced to express heavy or light chain was collected, and centrifuged at 8000 g for 10 min at 4° C., and the cells were washed once with 10 ml of PBS, and then vigorously shaken in 5 ml of BugBuster Master Mix Extraction Reagents (Merck) for resuspending the cells. The suspension was incubated for 20 min at room temperature, and then centrifuged at 6000 g for 15 min at 4° C. The supernatant was discarded to collect inclusion bodies.

The above inclusion bodies was resuspended in 5 ml BugBuster Master Mix and incubated vortically at room temperature for 5 min. 30 ml of 10 time-diluted BugBuster was added, mixed, and centrifuged at 6000 g for 15 min at 4° C. The supernatant was discarded, 30 ml of 10 time-diluted BugBuster was added to resuspend the inclusion body, mixed, and centrifuged twice at 6000 g at 4° C. for 15 min. 30 ml of 20 mM Tris-HCl pH 8.0 was added to resuspend the inclusion bodies, mixed, and centrifuged at 6000 g at 4° C. for 15 min. Finally, inclusion bodies were dissolved in 20 mM Tris-HCl 8M urea, and the purity of inclusion bodies was determined by SDS-PAGE and the concentration was measured by BCA kit.

b. Refolding

Synthesized short peptide KASEKIFYV (SEQ ID NO: 9) (Beijing Saibaisheng Gene Technology Co., Ltd.) were dissolved in DMSO to a concentration of 20 mg/ml. Inclusion bodies of light and heavy chains were solubilized in 8 M urea, 20 mM Tris pH 8.0, 10 mM DTT, and further denatured by adding 3 M guanidine hydrochloride, 10 mM sodium acetate, 10 mM EDTA before refolding. KASEKIFYV (SEQ ID NO: 9) peptide was added to a refolding buffer (0.4 M L-arginine, 100 mM Tris pH 8.3, 2 mM EDTA, 0.5 mM oxidized glutathione, 5 mM reduced glutathione, 0.2 mM PMSF, cooled to 4° C.) at 25 mg/L (final concentration). Then 20 mg/L of light chain and 90 mg/L of heavy chain (final concentration, heavy chain was added in three portions, 8 h/portion) were successively added, and refolded at 4° C. for at least 3 days to completion of refolding, and SDS-PAGE was used to confirm refolding.

c. Purification Upon Refolding

The refolding buffer was replaced with 10 volumes of 20 mM Tris pH 8.0 for dialysis, and the buffer was exchanged for at least two times to substantially reduce the ionic strength of the solution. After dialysis, the protein solution was filtered through a 0.45 μm cellulose acetate filter and loaded onto a HiTrap Q HP (GE, General Electric Company) anion exchange column (5 ml bed volume). The protein was eluted with a linear gradient of 0-400 mM NaCl prepared in 20 mM Tris pH 8.0 using Akta Purifier (GE), and the pMHC was eluted at approximately 250 mM NaCl. Peak fractions were collected and the purity thereof was detected by SDS-PAGE.

d. Biotinylation

Purified pMHC molecules were concentrated in a Millipore ultrafiltration tube, while the buffer was replaced with 20 mM Tris pH 8.0, and then biotinylation reagent 0.05 M Bicine pH 8.3, 10 mM ATP, 10 mM MgOAc, 50 μM D-Biotin, 100 μg/ml BirA enzyme (GST-BirA) was added. The resulting mixture was incubated at room temperature overnight, and SDS-PAGE was used to detect the completion of biotinylation.

e. Purification of Biotinylated Complex

The biotinylated and labeled pMHC molecules were concentrated to 1 ml in a Millipore ultrafiltration tube. The biotinylated pMHC was purified by gel filtration chromatography. 1 ml of concentrated biotinylated pMHC molecules was loaded on a HiPrep™ 16/60S200 HR column (GE) pre-equilibrated with filtered PBS using an Akta Purifier (GE) and eluted with PBS at a flow rate of 1 ml/min. The biotinylated pMHC molecules were eluted as a single peak at about 55 ml. The protein-containing fractions were combined and concentrated in a Millipore ultrafiltration tube. The concentration of protein was determined by BCA method (Thermo), protease inhibitor cocktail (Roche) was added and the biotinylated pMHC molecules were dispensed and stored at −80° C.

Figure 13:
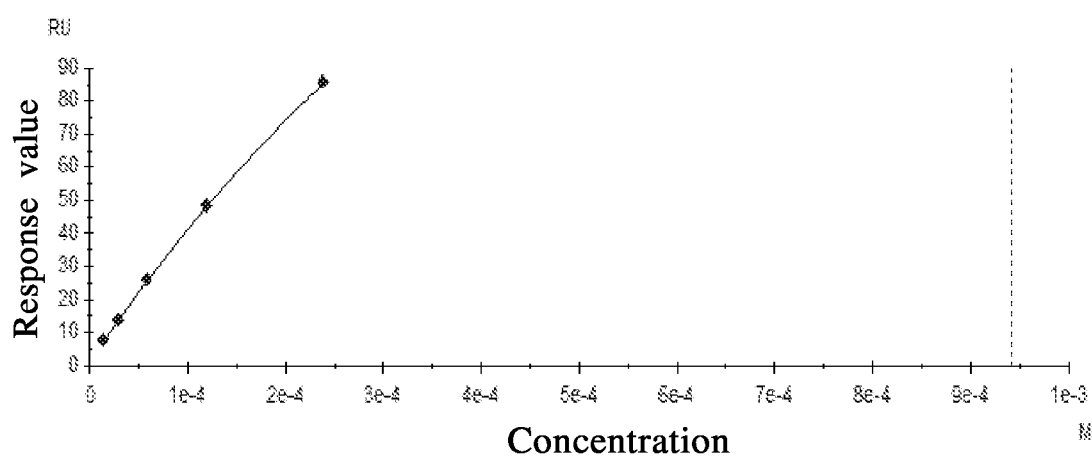
FIG. 13 is a BIAcore kinetic map of the binding of the soluble single-chain TCR of the present invention to KASEKIFYV-HLA A0201 complex.

The kinetic patterns of the soluble TCR molecules of the present invention and the soluble single-chain TCR molecules constructed in the present invention binding to the KASEKIFYV-HLA A0201 complex obtained by using BIAcore Evaluation software to calculate kinetic parameters are shown in FIG. 12 and FIG. 13, respectively. The pattern shows that both the soluble TCR molecules and soluble single-chain TCR molecules obtained in the present invention can bind to the KASEKIFYV-HLA A0201 complex. The above method was also used to detect the binding activity of the soluble TCR molecule of the present invention to complexes of several other unrelated antigen short peptides with HLA, and the results showed that the TCR molecule of the present invention did not bind to other unrelated antigens.

Example 7. Activation Experiment of T Cell Transduced with TCR of the Present Invention ELISPOT Protocol The following experiments were performed to prove the specific activation response of T cells transduced by TCR of the present invention to target cells. The production of IFN-γ detected by ELISPOT assay was used as the readout value of T cell activation.

Reagents

Assay medium: 10% FBS(Gibco, Cat No., 16000-044), RPMI 1640(Gibco, Cat No., C11875500bt)

Washing buffer (PBST): 0.01M PBS/0.05% Tween 20

PBS (Gibco, Cat No., C10010500BT)

PVDF ELISPOT 96 well-plate (Merck Millipore., Cat No., MSIPS4510)

Human IFN-γ ELISPOT PVDF-Enzyme Kit (BD) contains all the other necessary reagents (capture and detection antibody, streptavidin-alkaline phosphatase and BCIP/NBT solution)

Method

Preparation of Target Cells

The target cells used in this experiment were T2 cells loaded with specific short peptides. The target cells were prepared in the assay medium: the concentration of target cells wase adjusted to $2.0 \times 10^5$ cells/ml, and 100 microliters was added into each well to obtain $2.0 \times 10^4$ cells/well.

Preparation of Effector Cells

The effector cells (T cells) in this experiment were CD8$^+$ T cells transfected with TCR of the present invention specific to the SSX2 antigen short peptide, and CD8$^+$ T cells not transfected with the TCR of the present invention from the same volunteer were used as the control group. The T cells were stimulated with anti-CD3/CD28 coated beads (T cell amplification, life technologies), transduced with a lentivirus carrying the gene of TCR specific for SSX2 antigen short peptide, and expanded in 1640 medium containing 50 IU/ml of IL-2, 10 ng/ml of IL-7 and 10% FBS until 9-12 days after transduction. And then the cells were placed in the assay medium and washed by centrifugation at 300 g at room temperature for 10 minutes. The cells were then resuspended in the assay medium at 2× the desired final concentration. The negative control effector cells were treated in the same way.

Preparation of Solution of Short Peptide

The corresponding short peptide was added to the corresponding target cell (T2) assay group, so that the final concentration of the short peptide in the ELISPOT plate was 0.1 µg/ml.

ELISPOT

According to the manufacturer's instructions, the plate was prepared as follows: the anti-human IFN-γ capture antibody was diluted at 1:200 with 10 ml of sterile PBS per plate, and then aliquots of 100 microliters of the diluted capture antibody were added to each well. The plate was incubated overnight at 4° C. After incubation, the plate was washed to remove excess of capture antibody. 100 µl/well of RPMI 1640 medium containing 10% FBS was added, and the plate was incubated at room temperature for 2 hours to block the plate. Then the medium was washed away from the plate, and any remaining wash buffer was removed by tapping the ELISPOT plate on a piece of paper.

Then the assay components were added to the ELISPOT plate in the following order:

100 microliters of target cells $2*10^5$ cells/ml (so as to get a total of about $2*10^4$ target cells/well).

100 microliters of effector cells ($1*10^4$ effector cells/well and SSX2 TCR positive T cell/well).

All wells were prepared in duplicate.

Then the plate was incubated overnight (37° C./5% CO2). The next day, the medium was discarded, the plate was washed twice with double distilled water, then washed for three times with washing buffer, tapped on a piece of paper towel to remove residual washing buffer. Then the detection antibody was diluted at 1:200 with PBS containing 10% FBS, and added to each well at 100 µl/well. The plate was incubated at room temperature for 2 hours, then washed for 3 times with washing buffer, and tapped on a piece of paper towel to remove excess washing buffer.

Streptavidin-alkaline phosphatase was diluted at 1:100 with PBS containing 10% FBS, 100 microliters of diluted streptavidin-alkaline phosphatase was added to each well and the plate was incubated at room temperature for 1 hour. Then the plate was washed for 4 times with washing buffer, washed for 2 times with PBS, and tapped on a piece of paper towel to remove excess washing buffer and PBS. After washing, 100 µl/well of BCIP/NBT solution provided in the kit was added for development. During development, the plate was covered with a tin foil so as to keeping it in darkness, and let it stand for 5-15 minutes. During this period, the spots of the developing plate were routinely checked to determine the best time to quench the reaction. The BCIP/NBT solution was removed and the plate was rinsed with double distilled water to quench the development reaction, and spin-dried. Then the bottom of the well plate was removed, the plate was dried at room temperature until each well was completely dry. And then the immunospot plate counter (CTL, Cellular Technology Limited) was used to count the spots formed on the bottom membrane of the plate.

Results

The ELISPOT experiment (as described above) was used to test the release of IFN-γ from the T cells transduced with the TCR of the present invention in response to target cells loaded with SSX2 antigen short peptide KASEKIFYV (SEQ ID NO: 9). Graphpad prism6 was used to plot the number of ELSPOT spots observed in each well.

Figure 15:
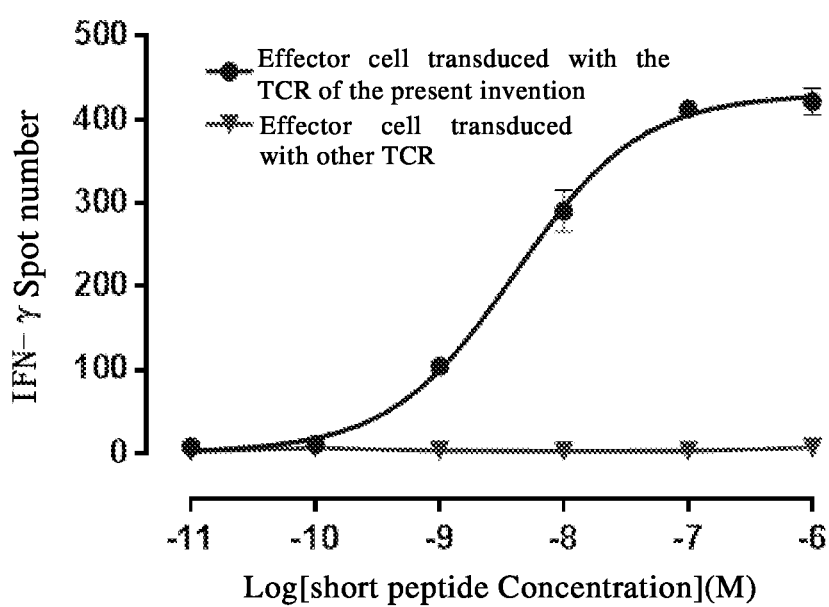
FIG. 15 shows the results of the ELISPOT activation function verification of the effector cells transduced with the TCR of the present invention.

The results of the experiment are shown in FIG. 15. The T cells transduced with the TCR of the present invention exhibit a good activation response to the target cells loaded with the specific short peptide, while the T cells not transduced with the TCR of the present invention exhibit basically no activation response to the corresponding target cells.

All documents mentioned in the present application are hereby incorporated by reference in their entireties, as if each is incorporated by reference. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A T cell receptor (TCR) that can bind to the KASEKIFYV-HLA A0201 complex, the TCR comprises a TCR α chain variable domain and a TCR β chain variable domain, 3 complementarity determining regions (CDR) of the TCR α chain variable domain are:

α CDR1- (SEQ ID NO: 10)
TSESDYY

α CDR2- (SEQ ID NO: 11)
QEAYKQQN

-continued

α CDR3- (SEQ ID NO: 12)
AYRSGIIQGAQKLV;

and 3 complementarity determining regions of the TCR β chain variable domain are:

β CDR1- (SEQ ID NO: 13)
PRHDT

-continued

β CDR2-
(SEQ ID NO: 14)
FYEKMQ

β CDR3-
(SEQ ID NO: 15)
ASSSDRELLFYNEQF.

2. The TCR of claim 1, wherein the TCR comprises a TCR α chain variable domain and a TCR β chain variable domain, and the TCR α chain variable domain is an amino acid sequence having at least 90% sequence identity with SEQ ID NO: 1; and/or the TCR β chain variable domain is an amino acid sequence with at least 90% sequence identity with SEQ ID NO: 5.

3. The TCR of claim 1, wherein the TCR comprises a TCR α chain variable domain, the amino acid sequence of which is SEQ ID NO: 1; wherein the TCR comprises a TCR β chain variable domain, the amino acid sequence of which is SEQ ID NO: 5.

4. The TCR of claim 1, wherein the TCR is a αβ heterodimer comprising a TCR α chain constant region TRAC*01 and a TCR β chain constant region TRBC1*01 or TRBC2*01.

5. The TCR of claim 4, wherein the amino acid sequence of the TCR α chain is SEQ ID NO: 3 and/or the amino acid sequence of the TCR β chain is SEQ ID NO: 7.

6. The TCR of claim 1, wherein the TCR is soluble.

7. The TCR of claim 6, wherein the TCR is a single-chain TCR.

8. The TCR of claim 7, wherein the TCR has one or more mutations at amino acid position 11, 13, 19, 21, 53, 76, 89, 91, or 94 of the α chain variable region, and/or at the last 3, 5 or 7 amino acid position of the short peptide of the α chain J gene; and/or the TCR has one or more mutations at amino acid position 11, 13, 19, 21, 53, 76, 89, 91, or 94 of the β chain variable region, and/or at the last 2, 4, or 6 amino acid position of the short peptide of the β chain J gene, wherein the amino acid position number is based on the position number listed in IMGT® (International Immunogenetics Information System).

9. The TCR of claim 8, wherein the amino acid sequence of the α chain variable domain of the TCR comprises SEQ ID NO: 32 and/or the amino acid sequence of the β chain variable domain of the TCR comprises SEQ ID NO: 34.

10. The TCR of claim 9, wherein the amino acid sequence of the TCR is SEQ ID NO: 30.

11. The TCR of claim 6, wherein the TCR comprises (a) all or part of the TCR α chain except for its transmembrane domain, and (b) all or part of the TCR β chain except for its transmembrane domain;
and each of (a) and (b) comprise the functional variable domain, or the functional variable domain and at least a portion of the constant domain of the TCR chain, respectively.

12. The TCR of claim 11, wherein cysteine residues form an artificial disulfide bond between the α and β chain constant domains of the TCR.

13. The TCR of claim 12, wherein the amino acid sequence of the TCR α chain is SEQ ID NO: 26 and/or the amino acid sequence of the TCR β chain is SEQ ID NO: 28.

14. The TCR of claim 11, wherein an artificial interchain disulfide bond is contained between α chain variable region and β chain constant region of the TCR.

15. The TCR of claim 14, wherein the TCR comprises α chain variable domain and β chain variable domain as well as all or part of β chain constant domains except for its transmembrane domain, however it does not comprise α chain constant domain, and α chain variable domain and β chain of the TCR form a heterodimer.

16. The TCR of claim 1, wherein a conjugate binds to the α chain and/or chain of the TCR at C- or N-terminal.

17. A multivalent TCR complex, wherein the multivalent TCR complex comprises at least two TCR molecules, and at least one TCR molecule is the TCR of claim 1.

18. A cell, wherein the cell expresses the TCR of claim 1.

19. A pharmaceutical composition, comprising a pharmaceutically acceptable carrier, and the TCR of claim 1, a TCR complex, or a cell, wherein the the TCR complex comprises at least two TCR molecules and at least one TCR molecule is the TCR of claim 1, and the cell expresses the TCR of claim 1.

20. A method for treating a SSX2-related disease, 2 comprising administering an appropriate amount of the TCR of claim 1, a TCR complex, a cell, or a pharmaceutical composition to a subject in need thereof, wherein the TCR complex comprises at least two TCR molecules and at least one TCR molecule is the TCR of claim 1, the cell expresses the TCR of claim 1, and the pharmaceutical composition comprises a pharmaceutically acceptable carrier and the TCR of claim 1, the TCR complex or the cell.

21. The TCR of claim 7, wherein the TCR is formed by connecting the α chain variable domain and the β chain variable domain through a peptide linking sequence.

22. The TCR of claim wherein the cysteine residues forming the artificial interchain disulfide bond in the TCR are substituted for one or more groups of amino acids selected from the group consisting of:
Thr48 of TRAC*01 exon 1 and Ser57 of TRBC1*01 or TRBC2*01 exon 1;
Thr45 of TRAC*01 exon 1 and Ser77 of TRBC1*01 or TRBC2*01 exon 1;
Tyr10 of TRAC*01 exon 1 and Ser17 of TRBC1*01 or TRBC2*01 exon 1;
Thr45 of TRAC*01 exon 1 and Asp59 of TRBC1*01 or TRBC2*01 exon 1;
Ser15 of TRAC*01 exon 1 and Glu15 of TRBC1*01 or TRBC2*01 exon 1;
Arg53 of TRAC*01 exon 1 and Ser54 of TRBC1*01 or TRBC2*01 exon 1;
Pro89 of TRAC*01 exon 1 and Ala19 of TRBC1*01 or TRBC2*01 exon 1; and
Tyr10 of TRAC*01 exon 1 and Glu20 of TRBC1*01 or TRBC2*01 exon 1.

23. The TCR of claim 14, wherein cysteine residues forming the artificial interchain disulfide bond in the TCR are substituted for one or more groups of amino acids selected from the group consisting of:
amino acid at position 46 of TRAV and amino acid at position 60 of TRBC1*01 orTRBC2*01 exon 1;
amino acid at position 47 of TRAV and amino acid at position 61 of TRBC1*01 orTRBC2*01 exon 1;
amino acid at position 46 of TRAV and amino acid at position 61 of TRBC 1*01 or TRBC2*01 exon 1; and
amino acid at position 47 of TRAV and amino acid at position 60 of TRBC 1*01 orTRBC2*01 exon 1.

24. The TCR of claim 16, wherein the conjugate is a detectable label or a therapeutic agent.

25. The TCR of claim 24, wherein the therapeutic agent is an anti-CD3 antibody.

26. The TCR of claim 18, wherein the cell is a T cell or stem cell.

* * * * *